US011154320B2

(12) United States Patent
Haverkost et al.

(10) Patent No.: US 11,154,320 B2
(45) Date of Patent: Oct. 26, 2021

(54) CUTTING BALLOON BASKET

(71) Applicant: BOSTON SCIENTIFIC SCIMED, INC., Maple Grove, MN (US)

(72) Inventors: Patrick A. Haverkost, Corcoran, MN (US); Joel N. Groff, Delano, MN (US); Joel M. Wasdyke, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 113 days.

(21) Appl. No.: 16/377,707

(22) Filed: Apr. 8, 2019

(65) Prior Publication Data

US 2019/0307992 A1    Oct. 10, 2019

Related U.S. Application Data

(60) Provisional application No. 62/654,756, filed on Apr. 9, 2018.

(51) Int. Cl.
*A61B 17/3207*   (2006.01)
*A61B 17/22*   (2006.01)
*A61M 25/10*   (2013.01)

(52) U.S. Cl.
CPC . *A61B 17/320725* (2013.01); *A61M 25/1002* (2013.01); *A61M 25/104* (2013.01); *A61B 2017/22001* (2013.01); *A61B 2017/22051* (2013.01); *A61B 2017/22061* (2013.01); *A61M 2025/109* (2013.01); *A61M 2025/1086* (2013.01)

(58) Field of Classification Search
CPC .......... A61B 2017/320048; A61B 17/320725; A61B 2017/22001; A61B 2017/22061; A61M 25/104; A61M 2025/109; A61M 2025/1086; A61F 2/958; A61F 2002/9583
See application file for complete search history.

(56) References Cited

U.S. PATENT DOCUMENTS

| | | | |
|---|---|---|---|
| 3,540,431 A | 11/1970 | Mobin-Uddin |
| 3,837,345 A | 9/1974 | Matar |
| 3,952,747 A | 4/1976 | Kimmel, Jr. |
| 4,273,128 A | 6/1981 | Lary |
| 4,425,908 A | 1/1984 | Simon |
| 4,494,531 A | 1/1985 | Gianturco |

(Continued)

FOREIGN PATENT DOCUMENTS

| DE | 3402573 A1 | 8/1985 |
|---|---|---|
| EP | 1453414 A2 | 6/2003 |

(Continued)

OTHER PUBLICATIONS

International Search Report and Written Opinion dated Jun. 26, 2019 for International Application No. PCT/US2019/026327.

*Primary Examiner* — Tan-Uyen T Ho
*Assistant Examiner* — Bridget E. Rabaglia
(74) *Attorney, Agent, or Firm* — Seager, Tufte & Wickhem LLP

(57) ABSTRACT

A cutting balloon catheter including a balloon mounted on a distal portion of a catheter shaft. An expandable frame may be disposed over the balloon. The expandable frame may include a plurality of struts extending from a proximal end region to a distal end region. One or more cutting members may be secured to the expandable frame.

19 Claims, 15 Drawing Sheets

(56) References Cited

U.S. PATENT DOCUMENTS

| | | |
|---|---|---|
| 4,619,246 A | 10/1986 | Molgaard-Nielsen et al. |
| 4,643,184 A | 2/1987 | Mobin-Uddin |
| 4,650,466 A | 3/1987 | Luther |
| 4,696,667 A | 9/1987 | Masch |
| 4,723,549 A | 2/1988 | Wholey et al. |
| 4,728,319 A | 3/1988 | Masch |
| 4,765,332 A | 8/1988 | Fischell et al. |
| 4,817,600 A | 4/1989 | Herms et al. |
| 4,832,055 A | 5/1989 | Palestrant |
| 4,840,176 A | 6/1989 | Ohno |
| 4,990,156 A | 2/1991 | Lefebvre |
| 4,998,539 A | 3/1991 | Delsanti |
| 5,009,659 A | 4/1991 | Hamlin et al. |
| 5,030,201 A | 7/1991 | Palestrant |
| 5,035,706 A | 7/1991 | Giantureo et al. |
| 5,047,040 A | 9/1991 | Simpson et al. |
| 5,069,679 A | 12/1991 | Taheri |
| 5,078,722 A | 1/1992 | Stevens |
| 5,152,773 A | 10/1992 | Redha |
| 5,176,693 A | 1/1993 | Pannek, Jr. |
| 5,196,024 A | 3/1993 | Barath |
| 5,209,749 A | 5/1993 | Buelna |
| 5,217,484 A | 6/1993 | Marks |
| 5,226,909 A | 7/1993 | Evans et al. |
| 5,250,059 A | 10/1993 | Andreas et al. |
| 5,282,813 A | 2/1994 | Redha |
| 5,287,858 A | 2/1994 | Hammerslag et al. |
| 5,320,634 A | 6/1994 | Vigil et al. |
| 5,324,304 A | 6/1994 | Rasmussen |
| 5,329,942 A | 7/1994 | Gunther et al. |
| 5,336,234 A | 8/1994 | Vigil et al. |
| 5,354,279 A | 10/1994 | Hoefling |
| 5,370,657 A | 12/1994 | Irie |
| 5,372,601 A | 12/1994 | Lary |
| 5,375,612 A | 12/1994 | Cottonceau et al. |
| 5,383,887 A | 1/1995 | Nadal |
| 5,417,703 A | 5/1995 | Brown et al. |
| 5,441,510 A | 8/1995 | Simpson et al. |
| 5,507,760 A | 4/1996 | Wynne et al. |
| 5,507,761 A | 4/1996 | Duer |
| 5,522,825 A | 6/1996 | Kropf et al. |
| 5,569,277 A | 10/1996 | Evans et al. |
| 5,601,595 A | 2/1997 | Smith |
| 5,616,149 A | 4/1997 | Barath |
| 5,628,746 A | 5/1997 | Clayman |
| 5,628,761 A | 5/1997 | Rizik |
| 5,634,942 A | 6/1997 | Chevillon et al. |
| 5,643,296 A | 7/1997 | Hundertmark et al. |
| 5,649,953 A | 7/1997 | Lefebvre |
| 5,709,704 A | 1/1998 | Nott et al. |
| 5,713,913 A | 2/1998 | Lary et al. |
| 5,725,543 A | 3/1998 | Redha |
| 5,797,935 A | 8/1998 | Barath |
| 5,810,874 A | 9/1998 | Lefebrve |
| 5,836,968 A | 11/1998 | Simon et al. |
| 5,836,969 A | 11/1998 | Kim et al. |
| 5,843,103 A | 12/1998 | Wulfman |
| 5,853,420 A | 12/1998 | Chevillon et al. |
| 5,895,402 A | 4/1999 | Hundertmark et al. |
| 5,902,313 A | 5/1999 | Redha |
| 5,947,985 A | 9/1999 | Imran |
| 5,968,071 A | 10/1999 | Chevillo et al. |
| 5,976,172 A | 11/1999 | Homsma et al. |
| 6,009,877 A | 1/2000 | Edwards |
| 6,013,093 A | 1/2000 | Nott et al. |
| 6,102,938 A | 8/2000 | Evans et al. |
| 6,165,187 A | 12/2000 | Reger |
| 6,238,412 B1 | 5/2001 | Dubrul et al. |
| 6,241,746 B1 | 6/2001 | Bosma et al. |
| 6,258,108 B1 | 7/2001 | Lary |
| 6,267,776 B1 | 7/2001 | O'Connell |
| 6,331,166 B1 | 12/2001 | Burbank et al. |
| 6,423,032 B2 | 7/2002 | Parodi |
| 6,451,036 B1 | 9/2002 | Heitzmann et al. |
| 6,500,186 B2 | 12/2002 | Lafontaine et al. |
| 6,508,773 B2 | 1/2003 | Burbank et al. |
| 6,547,803 B2 | 4/2003 | Seward et al. |
| 6,562,062 B2 | 5/2003 | Jenusaitis et al. |
| 6,632,231 B2 | 10/2003 | Radisch, Jr. |
| 6,709,444 B1 | 3/2004 | Makower |
| 6,746,463 B1 | 6/2004 | Schwartz |
| 6,808,531 B2 | 10/2004 | Lafontaine et al. |
| 6,942,680 B2 | 9/2005 | Grayzel et al. |
| 6,951,566 B2 | 10/2005 | Lary |
| 7,011,670 B2 | 3/2006 | Radisch, Jr. |
| 7,029,483 B2 | 4/2006 | Schwartz |
| 7,131,981 B2 | 11/2006 | Appling et al. |
| 7,153,315 B2 | 12/2006 | Miller |
| 7,279,002 B2 | 1/2007 | Shaw et al. |
| 7,172,609 B2 | 2/2007 | Radisch, Jr. |
| 7,201,761 B2 | 4/2007 | Woolfson et al. |
| 7,270,673 B2 | 9/2007 | Yee et al. |
| 7,291,158 B2 | 11/2007 | Crow et al. |
| 7,303,572 B2 | 12/2007 | Melsheimer et al. |
| 7,338,463 B2 | 3/2008 | Vigil |
| 7,396,358 B2 | 7/2008 | Appling et al. |
| 7,413,558 B2 | 8/2008 | Kelley et al. |
| 7,494,497 B2 | 2/2009 | Weber |
| 7,517,352 B2 | 4/2009 | Evans et al. |
| 7,566,319 B2 | 7/2009 | McAuley et al. |
| 7,658,744 B2 | 2/2010 | Jackson |
| 7,662,163 B2 | 2/2010 | Grayzel et al. |
| 7,691,119 B2 | 4/2010 | Farnan |
| 7,753,907 B2 | 7/2010 | DiMatteo et al. |
| 7,754,047 B2 | 7/2010 | Kelley |
| 7,758,604 B2 | 7/2010 | Wu et al. |
| 7,799,043 B2 | 9/2010 | O'Brien et al. |
| 8,038,691 B2 | 1/2011 | Bence et al. |
| 7,879,053 B2 | 2/2011 | Trinidad |
| 7,883,537 B2 | 2/2011 | Grayzel et al. |
| 7,993,358 B2 | 8/2011 | O'Brien |
| 8,043,311 B2 | 10/2011 | Radisch, Jr. et al. |
| 8,048,093 B2 | 11/2011 | Mapes et al. |
| 8,052,703 B2 | 11/2011 | St. Martin et al. |
| 8,066,726 B2 | 11/2011 | Kelley |
| 8,080,026 B2 | 12/2011 | Konstantino et al. |
| 8,172,864 B2 | 5/2012 | Wu |
| 8,211,354 B2 | 7/2012 | Burton |
| 8,323,243 B2 | 12/2012 | Schneider et al. |
| 8,323,307 B2 | 12/2012 | Hardert |
| 8,361,096 B2 | 1/2013 | Bence et al. |
| 8,454,636 B2 | 6/2013 | Konstantino et al. |
| 8,454,637 B2 | 6/2013 | Aggerholm et al. |
| 8,491,615 B2 | 7/2013 | Manderfeld et al. |
| 8,523,887 B2 | 9/2013 | Grayzel et al. |
| 8,690,903 B2 | 4/2014 | Bence et al. |
| 8,870,816 B2 | 10/2014 | Chambers et al. |
| 9,095,688 B2 | 8/2015 | Burton |
| 9,179,936 B2 | 11/2015 | Feld et al. |
| 9,199,066 B2 | 12/2015 | Konstantino et al. |
| 9,211,394 B2 | 12/2015 | Leffel |
| 9,216,033 B2 | 12/2015 | Feld et al. |
| 9,302,071 B2 | 4/2016 | Manderfeld et al. |
| 9,364,255 B2 | 6/2016 | Weber |
| 9,375,328 B2 | 6/2016 | Farnan |
| 9,604,036 B2 | 3/2017 | Burton et al. |
| 9,763,691 B2 | 9/2017 | Spencer et al. |
| 2003/0042186 A1* | 3/2003 | Boyle ................ A61F 2/01 <br> 210/136 |
| 2003/0144683 A1 | 7/2003 | Sirhan et al. |
| 2003/0163148 A1 | 8/2003 | Wang et al. |
| 2004/0034384 A1* | 2/2004 | Fukaya ............ A61M 25/104 <br> 606/191 |
| 2004/0127920 A1 | 7/2004 | Radisch, Jr. |
| 2004/0204738 A1 | 10/2004 | Weber et al. |
| 2005/0021071 A1 | 1/2005 | Konstantino et al. |
| 2005/0070888 A1 | 3/2005 | Dimatteo et al. |
| 2005/0119678 A1 | 6/2005 | O'Brien et al. |
| 2005/0137615 A1 | 6/2005 | Mapes et al. |
| 2005/0149102 A1 | 7/2005 | Radisch, Jr. et al. |
| 2005/0288629 A1 | 12/2005 | Kunis |
| 2006/0085026 A1 | 4/2006 | Appling et al. |
| 2006/0111736 A1 | 5/2006 | Kelley |
| 2006/0116700 A1 | 6/2006 | Crow |

(56) References Cited

U.S. PATENT DOCUMENTS

| | | |
|---|---|---|
| 2006/0116701 A1 | 6/2006 | Crow |
| 2006/0129093 A1 | 6/2006 | Jackson |
| 2006/0135980 A1 | 6/2006 | Trinidad |
| 2006/0178685 A1 | 8/2006 | Melsheimer |
| 2006/0182873 A1 | 8/2006 | Klisch et al. |
| 2006/0247674 A1 | 11/2006 | Roman |
| 2007/0016232 A1 | 1/2007 | St. Martin et al. |
| 2007/0060863 A1 | 3/2007 | Goeken et al. |
| 2007/0213752 A1 | 9/2007 | Hack |
| 2008/0077164 A1 | 3/2008 | Murphy |
| 2008/0306499 A1 | 12/2008 | Katoh et al. |
| 2009/0099581 A1 | 4/2009 | Kim et al. |
| 2009/0171283 A1 | 7/2009 | Schaffer et al. |
| 2009/0171284 A1 | 7/2009 | Burke et al. |
| 2010/0042121 A1 | 2/2010 | Schneider et al. |
| 2010/0241148 A1 | 9/2010 | Schon et al. |
| 2010/0324472 A1 | 12/2010 | Wulfman |
| 2012/0191111 A1 | 7/2012 | Aggerholm et al. |
| 2013/0041391 A1 | 2/2013 | Spencer et al. |
| 2014/0378966 A1 | 12/2014 | Haverkost et al. |
| 2015/0057657 A1 | 2/2015 | Squire et al. |
| 2017/0080192 A1 | 3/2017 | Giasolli et al. |
| 2017/0100570 A1* | 4/2017 | Giasolli .............. B29C 48/0022 |
| 2018/0043140 A1 | 2/2018 | Iwano et al. |
| 2018/0304052 A1* | 10/2018 | Schneider ......... A61M 25/1002 |

FOREIGN PATENT DOCUMENTS

| | | |
|---|---|---|
| WO | 0160262 A1 | 8/2001 |
| WO | 03049603 A2 | 6/2003 |
| WO | 03049603 A3 | 10/2003 |
| WO | 2012071095 A1 | 5/2012 |
| WO | 2016163495 A1 | 10/2016 |

* cited by examiner

CUTTING BALLOON BASKET

CROSS REFERENCE TO RELATED APPLICATIONS

This application claims the benefit of priority to Provisional Application No. 62/654,756, filed Apr. 9, 2018, the entire disclosure of which is hereby incorporated by reference.

TECHNICAL FIELD

The disclosure is directed to angioplasty balloon catheters including one or more cutting blades mounted to the balloon. More particularly, the disclosure is directed to cutting blades of a cutting balloon catheter having a basket.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action, or lack of oxygenation and/or circulation to other regions of the body.

Occluded, stenotic, or narrowed blood vessels, as well as native or synthetic arteriovenous dialysis fistulae, may be treated in a recanalization procedure, such as with an angioplasty balloon catheter advanced over a guidewire to an occlusion so that the balloon is positioned across the occlusion. The balloon is then inflated to enlarge the passageway through the occlusion.

One of the major obstacles in treating coronary artery disease and/or treating blocked blood vessels or fistulae is re-stenosis or re-narrowing of the passageway through the occlusion subsequent to an angioplasty procedure or other recanalization procedure. Evidence has shown that cutting or scoring the stenosis, for example, with an angioplasty balloon equipped with a cutting element, during treatment can reduce incidence of re-stenosis. Additionally, cutting or scoring the stenosis may reduce trauma at the treatment site and/or may reduce the trauma to adjacent healthy tissue. Cutting elements may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting elements having cutting edges have been developed to attempt to enhance angioplasty treatments. Depending on the level of plaque (thickness and length) in peripheral vessels it may be difficult for a physician to expand the internal diameter of the vessel sufficiently to successfully restore blood flow. The compliance of the vessel may need to be improved such that an inflated balloon will cause an expansion in the internal diameter of the vessel that will remain after the balloon is removed.

Accordingly, there is an ongoing need for improved cutting elements, such as cutting blades, and methods of mounting cutting elements onto an inflatable angioplasty balloon of an angioplasty balloon catheter which creates long, continuous disruptions in the plaque that creates a plane for the lesion to crack when the balloon is inflated. Namely, it would be desirable to provide a cutting member for use with an angioplasty balloon that will create a long cutting plane when the balloon is inflated.

SUMMARY

The disclosure is directed to several alternative designs, materials and methods of manufacturing medical device structures and assemblies, and the use thereof.

In a first example, a balloon catheter may comprise a catheter shaft, an inflatable balloon secured to a distal portion of the catheter shaft, the inflatable balloon including one or more channels formed in an outer surface thereof, an expandable frame disposed over the balloon and at least in part within the one or more channels, the expandable frame comprising a plurality of struts each having proximal section, a distal section, and an intermediate section, wherein the proximal section is pivotably coupled to the intermediate section and the distal section is pivotably coupled to the intermediate section, and one or more cutting members coupled to the expandable frame.

In another example, a balloon catheter may comprise a catheter shaft, an inflatable balloon secured to a distal portion of the catheter shaft, an expandable frame disposed over the balloon, the expandable frame comprising a plurality of struts each having proximal section, a distal section, and an intermediate section, wherein the proximal section is pivotably coupled to the intermediate section and the distal section is pivotably coupled to the intermediate section, and one or more cutting members coupled to the expandable frame.

Alternatively or additionally to any of the examples above, in another example, a plurality of elastomeric bands are circumferentially surrounding the expandable frame at longitudinally spaced apart locations along the balloon.

Alternatively or additionally to any of the examples above, in another example, the plurality of elastomeric bands are in tension when the balloon is in a fully deflated configuration.

Alternatively or additionally to any of the examples above, in another example, the plurality of elastomeric bands apply a radially inward force on the plurality of struts to press the plurality of struts against an outer surface of the balloon.

Alternatively or additionally to any of the examples above, in another example, each strut of the plurality of struts may include two or more cutting members.

Alternatively or additionally to any of the examples above, in another example, the one or more cutting members may be coupled to the intermediate section of the expandable frame.

Alternatively or additionally to any of the examples above, in another example, a distal end of the proximal section of the expandable frame may comprise at least one hook configured to pivotably couple with at least one aperture formed in the intermediate section.

Alternatively or additionally to any of the examples above, in another example, a proximal end of the distal section of the expandable frame may comprise at least one aperture configured to pivotably couple with at least one hook formed in the intermediate section.

Alternatively or additionally to any of the examples above, in another example, each intermediate section of the plurality of struts may have one or more mounting modules configured to receive the one or more cutting members.

Alternatively or additionally to any of the examples above, in another example, the intermediate section may comprise two or more links pivotably coupled together.

Alternatively or additionally to any of the examples above, in another example, each link of the two or more links may comprise a first end having a first coupling mechanism, a second end having a second coupling mechanism, and an intermediate region defining a channel for receiving a cutting member therein.

Alternatively or additionally to any of the examples above, in another example, the first coupling mechanism may comprise an aperture.

Alternatively or additionally to any of the examples above, in another example, the second coupling mechanism may comprise a hook.

Alternatively or additionally to any of the examples above, in another example, the link may be mechanically deformed to secure the cutting member within the channel.

Alternatively or additionally to any of the examples above, in another example, the intermediate section comprises two or more rails pivotably coupling adjacent mounting modules together.

Alternatively or additionally to any of the examples above, in another example, the rail has a width less than a width of the mounting modules.

Alternatively or additionally to any of the examples above, in another example, the cutting member may be adhesively secured to the link.

Alternatively or additionally to any of the examples above, in another example, the expandable frame may be secured to the catheter shaft adjacent to a proximal end of the expandable frame.

Alternatively or additionally to any of the examples above, in another example, the balloon catheter may further comprise a bumper secured to the catheter shaft distal to a distal end of the expandable frame.

Alternatively or additionally to any of the examples above, in another example, a depth of the one or more channels may be equal to or less than a thickness of the plurality of struts of the expandable frame.

Alternatively or additionally to any of the examples above, in another example, the links may be pivotably coupled via a rail.

Alternatively or additionally to any of the examples above, in another example, the links and the rail may form a monolithic structure.

Alternatively or additionally to any of the examples above, in another example, the rail may have a width less than a width of the links.

Alternatively or additionally to any of the examples above, in another example, the balloon may include one or more channels formed in an outer surface thereof.

Alternatively or additionally to any of the examples above, in another example, at least a portion of the expandable frame may be disposed within the one or more channels.

Alternatively or additionally to any of the examples above, in another example, the cutting member may be adhesively secured to the expandable frame.

Alternatively or additionally to any of the examples above, in another example, at least one of a proximal end region or a distal end region of the expandable frame may include a collar.

Alternatively or additionally to any of the examples above, in another example, the collar may include a helical cut extending from an outer surface to an inner surface of the collar.

Alternatively or additionally to any of the examples above, in another example, the collar includes a first end region, a second end region, and an intermediate region between the first and second end regions. The intermediate region includes a helical cut. The first end region is fixedly secured to the catheter shaft and the second end region is axially slidable relative to the catheter shaft. Ends of the plurality of struts are fixedly secured to the second end region of the collar.

In another example, a balloon catheter may comprise a catheter shaft, an inflatable balloon secured to a distal portion of the catheter shaft, the inflatable balloon including one or more channels formed in an outer surface thereof and an expandable frame disposed over the balloon and at least in part within the one or more channels. The expandable frame may comprise a proximal section having a proximal collar and a plurality of struts extending distally from the proximal collar, a distal section having a distal collar and a plurality of struts extending proximally from the distal collar, an intermediate section having a plurality of struts extending between the proximal section and the distal section, and at least one cutting member coupled to each strut of the plurality of struts of the intermediate section. The intermediate section may be pivotably coupled to the plurality of struts of the proximal section and pivotably coupled to the plurality of struts of the distal section. At least one of the proximal collar or distal collar may be fixedly secured to the catheter shaft and the other of the proximal collar or distal collar may be axially slidable along the catheter shaft.

Alternatively or additionally to any of the examples above, in another example, each strut of the plurality of struts the intermediate section may comprise two or more links pivotably coupled to one another.

Alternatively or additionally to any of the examples above, in another example, each link of the two or more links may comprise a first end having a first coupling mechanism, a second end having a second coupling mechanism, and an intermediate region defining a channel for receiving a cutting member therein.

Alternatively or additionally to any of the examples above, in another example, each strut of the plurality of struts of the intermediate section may comprise two or more mounting modules, each mounting module configured to carry a cutting member.

Alternatively or additionally to any of the examples above, in another example, a distal end of the proximal section of the expandable frame may comprise at least one hook configured to pivotably couple with at least one aperture formed in the intermediate section.

Alternatively or additionally to any of the examples above, in another example, a proximal end of the distal section of the expandable frame may comprise at least one aperture configured to pivotably couple with at least one hook formed in the intermediate section.

In another example, a balloon catheter may comprise a catheter shaft, an inflatable balloon secured to a distal portion of the catheter shaft, and an expandable frame disposed over the balloon. The expandable frame may comprise a proximal collar, a distal collar, a plurality of struts extending between the proximal collar and the distal collar, the plurality of struts including a proximal end region, a distal end region, and an intermediate region disposed therebetween and at least one cutting member coupled to each strut of the plurality of struts. The intermediate region may be pivotably coupled to the proximal end region and pivotably coupled to the distal end region and at least one of the proximal collar or distal collar may be fixedly secured to the catheter shaft and the other of the proximal collar or distal collar is axially slidable along the catheter shaft.

Alternatively or additionally to any of the examples above, in another example, each strut of the plurality of struts may comprise two or more links pivotably coupled to one another.

Alternatively or additionally to any of the examples above, in another example, each strut of the plurality of struts may comprise a monolithic structure.

Alternatively or additionally to any of the examples above, in another example, each strut of the plurality of struts may comprise two or more mounting modules, each mounting module configured to carry a cutting member.

Alternatively or additionally to any of the examples above, in another example, a distal end of the proximal end region of the struts may comprise at least one hook configured to pivotably couple with at least one aperture formed in the intermediate section.

Alternatively or additionally to any of the examples above, in another example, a proximal end of the distal end region of the struts may comprise at least one aperture configured to pivotably couple with at least one hook formed in the intermediate section.

In another example, a balloon catheter includes a catheter shaft, an inflatable balloon secured to a distal portion of the catheter shaft, and an expandable frame disposed over the balloon. The expandable frame includes a proximal collar positioned at a proximal end of the balloon, a distal collar positioned at a distal end of the balloon, a plurality of struts extending between the proximal collar and the distal collar, and at least one cutting member coupled to each strut of the plurality of struts. The plurality of struts including a proximal end region, a distal end region, and an intermediate region disposed therebetween. The intermediate region is pivotably coupled to the proximal end region and pivotably coupled to the distal end region. A first one of the proximal collar and distal collar includes a portion fixedly secured to the catheter shaft and a second one of the proximal collar and distal collar includes a portion axially slidable relative to the catheter shaft.

Alternatively or additionally to any of the examples above, in another example, each strut of the plurality of struts comprises a monolithic structure.

Alternatively or additionally to any of the examples above, in another example, the second one of the proximal collar and distal collar includes an intermediate region having a helical cut extending through a sidewall thereof, the intermediate region positioned between a first end region and a second end region thereof.

Alternatively or additionally to any of the examples above, in another example, the first end region is fixedly secured to the catheter shaft and the second end region is axially slidably relative to the catheter shaft.

Alternatively or additionally to any of the examples above, in another example, an axial length of the intermediate region changes when the second end region axially slides relative to the catheter shaft.

Alternatively or additionally to any of the examples above, in another example, ends of the plurality of struts are affixed to the second end region. In another example, a balloon catheter may comprise a catheter shaft, an inflatable balloon secured to a distal portion of the catheter shaft, the inflatable balloon including one or more channels formed in an outer surface thereof, and an expandable frame disposed over the balloon and at least in part within the one or more channels. The expandable frame may comprise a proximal section having a proximal collar and a plurality of struts extending distally from the proximal collar and each strut having a coupling mechanism positioned adjacent to a distal end thereof, a distal section having a distal collar and a plurality of struts extending proximally from the distal collar and each strut having a coupling mechanism positioned adjacent to a proximal end thereof, an intermediate section having a plurality of struts extending between the proximal section and the distal section, each strut having a first coupling mechanism positioned adjacent to a first end and configured to engage the coupling mechanism of the proximal section and a second coupling mechanism positioned adjacent to a second end and configured to engage the coupling mechanism of the distal section, and at least one cutting member coupled to each strut of the plurality of struts of the intermediate section.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The aspects of the disclosure may be more completely understood in consideration of the following detailed description of various embodiments in connection with the accompanying drawings, in which.

Figure 1:
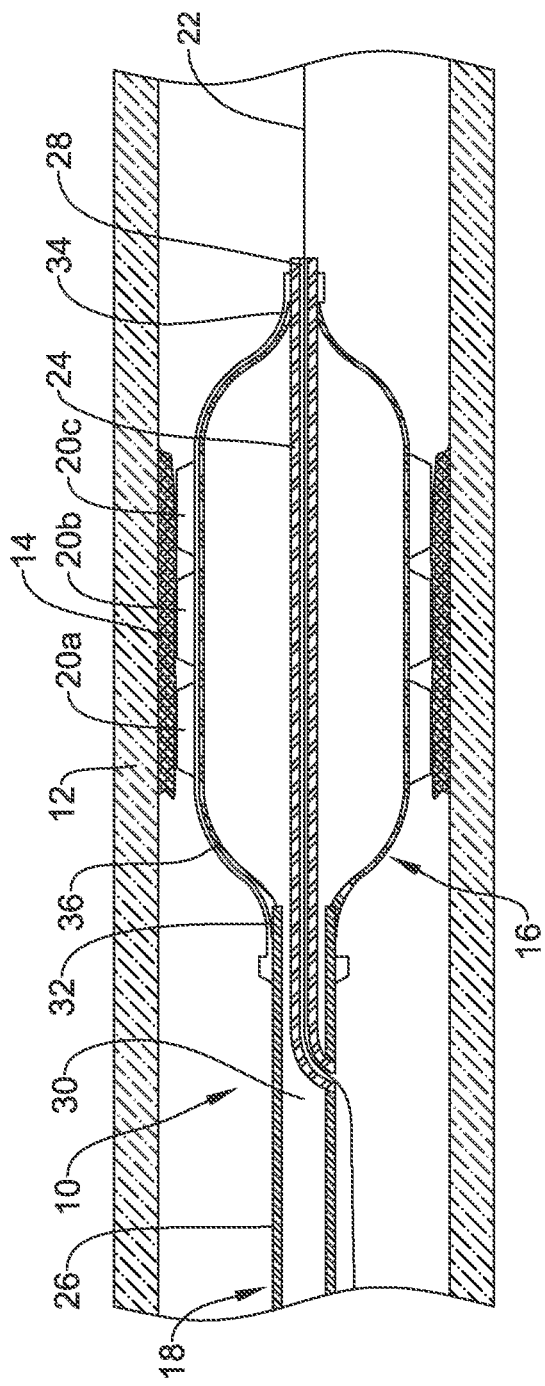
FIG. 1 is partial cross-sectional view of an exemplary cutting balloon catheter disposed in a blood vessel.

While the aspects of the disclosure amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

FIG. 1 is a partial cross-sectional side view of an illustrative catheter 10 disposed in a blood vessel 12 and positioned adjacent to an intravascular lesion 14. The catheter 10 may include a balloon 16 coupled to a catheter shaft 18. One or more cutting members or blades 20a, 20b, 20c (collectively, 20) may be mounted on the balloon 16. In some cases, the one or more cutting members 20 may be mounted on an expandable frame or basket 36 which, in turn, may be coupled to the balloon 16 and/or catheter shaft 18. In general, the catheter 10 may be advanced over a guidewire 22, through the vasculature, to a target area. Once positioned at the target location in the vasculature, the balloon 16 can be inflated to exert a radially outward force on the lesion 14, as the cutting members 20 engage the lesion 14. Thus, the cutting members 20 may cut or score the lesion 14 to facilitate enlarging the lumen proximate the lesion 14. The target area may be within any suitable peripheral or cardiac vessel lumen location.

The balloon 16 may have a length in the range of about 60 to 140 millimeters (mm), about 80 to 120 mm, or about 100 mm. In some instances, the balloon 16 may have an outer diameter in the range of about 4 to 12 mm, about 6 to 10 mm or about 8 mm. The cutting members 20 may vary in number, position, and arrangement about the balloon 16. For example, the catheter 10 may include one, two, three, four, five, six, or more cutting members 20 that are disposed at any position along the balloon 16 and in a regular, irregular, or any other suitable pattern. For example, in some embodiments the balloon 16 may include a plurality of cutting members 20 longitudinally arranged symmetrically around the circumference of the balloon 16.

The cutting members 20 may be made from any suitable material such as a metal, metal alloy, polymer, metal-polymer composite, and the like, or any other suitable material. For example, cutting members 20 may be made from stainless steel, titanium, nickel-titanium alloys, tantalum, iron-cobalt-nickel alloys, or other metallic materials in some instances.

The balloon 16 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyetherester, polyester, polyamide, elastomeric polyamides, polyether block amide (PEBA), as well as other suitable materials, or mixtures, combinations, copolymers thereof, polymer/metal composites, and the like. In some instances, the balloon 16 may include a single layer of material, whereas in other instances the balloon 16 may be of a multi-layer construction, including a plurality of layers of materials. For instance, the balloon 16 may be formed as a co-extrusion or tri-layer extrusion in some instances.

The balloon 16 may be configured so that the balloon 16 includes one or more "wings" or wing-shaped regions when the balloon 16 is deflated. In some instances, the wings may be configured so that the cutting members 20 can be positioned at the inward-most positions of the deflated balloon 16, with the wings of the balloon folds positioned between adjacent cutting members 20. This arrangement may reduce the exposure of the cutting members 20 to the blood vessel during delivery of the balloon 16 to the lesion 14.

The shaft 18 may be a catheter shaft, similar to typical catheter shafts. For example, the catheter shaft 18 may include an outer tubular member 26 and an inner tubular member 24 extending through at least a portion of the outer tubular member 26. The tubular members 24, 26 may be manufactured from a number of different materials. For example, the tubular members 24, 26 may be made of metals, metal alloys, polymers, metal-polymer composites or any other suitable materials.

The tubular members 24, 26 may be arranged in any appropriate way. For example, in some embodiments the inner tubular member 24 can be disposed coaxially within the outer tubular member 26. According to these embodiments, the inner and outer tubular members 24, 26 may or may not be secured to one another along the general longitudinal axis of the catheter shaft 18. Alternatively, the inner tubular member 24 may follow the inner wall or otherwise be disposed adjacent the inner wall of the outer tubular member 26. In other embodiments, the tubular members 24, 26 may be arranged in another desired fashion.

The inner tubular member 24 may include an inner lumen 28. In at least some embodiments, the inner lumen 28 is a guidewire lumen for receiving the guidewire 22 therethrough. Accordingly, the catheter 10 can be advanced over the guidewire 22 to the desired location. The guidewire lumen 28 may extend along essentially the entire length of the catheter shaft 18 such that catheter 10 resembles traditional "over-the-wire" catheters. Alternatively, the guidewire lumen 28 may extend along only a portion of the catheter shaft 18 such that the catheter 10 resembles "single-operator-exchange" or "rapid-exchange" catheters.

The catheter shaft 18 may also include an inflation lumen 30 that may be used, for example, to transport inflation media to and from the balloon 16 to selectively inflate and/or deflate the balloon 16. The location and position of the inflation lumen 30 may vary, depending on the configuration of the tubular members 24, 26. For example, when the outer tubular member 26 surrounds the inner tubular member 24, the inflation lumen 30 may be defined within the space between the tubular members 24, 26. In embodiments in which the outer tubular member 26 is disposed alongside the inner tubular member 24, then the inflation lumen 30 may be the lumen of the outer tubular member 26.

The balloon 16 may be coupled to the catheter shaft 18 in any of a number of suitable ways. For example, the balloon 16 may be adhesively or thermally bonded to the catheter shaft 18. In some embodiments, a proximal waist 32 of the balloon 16 may be bonded to the catheter shaft 18, for example, bonded to the distal end of the outer tubular member 26, and a distal waist 34 of the balloon 16 may be bonded to the catheter shaft 18, for example, bonded to the distal end of the inner tubular member 24. The exact bonding positions, however, may vary.

Figure 2:
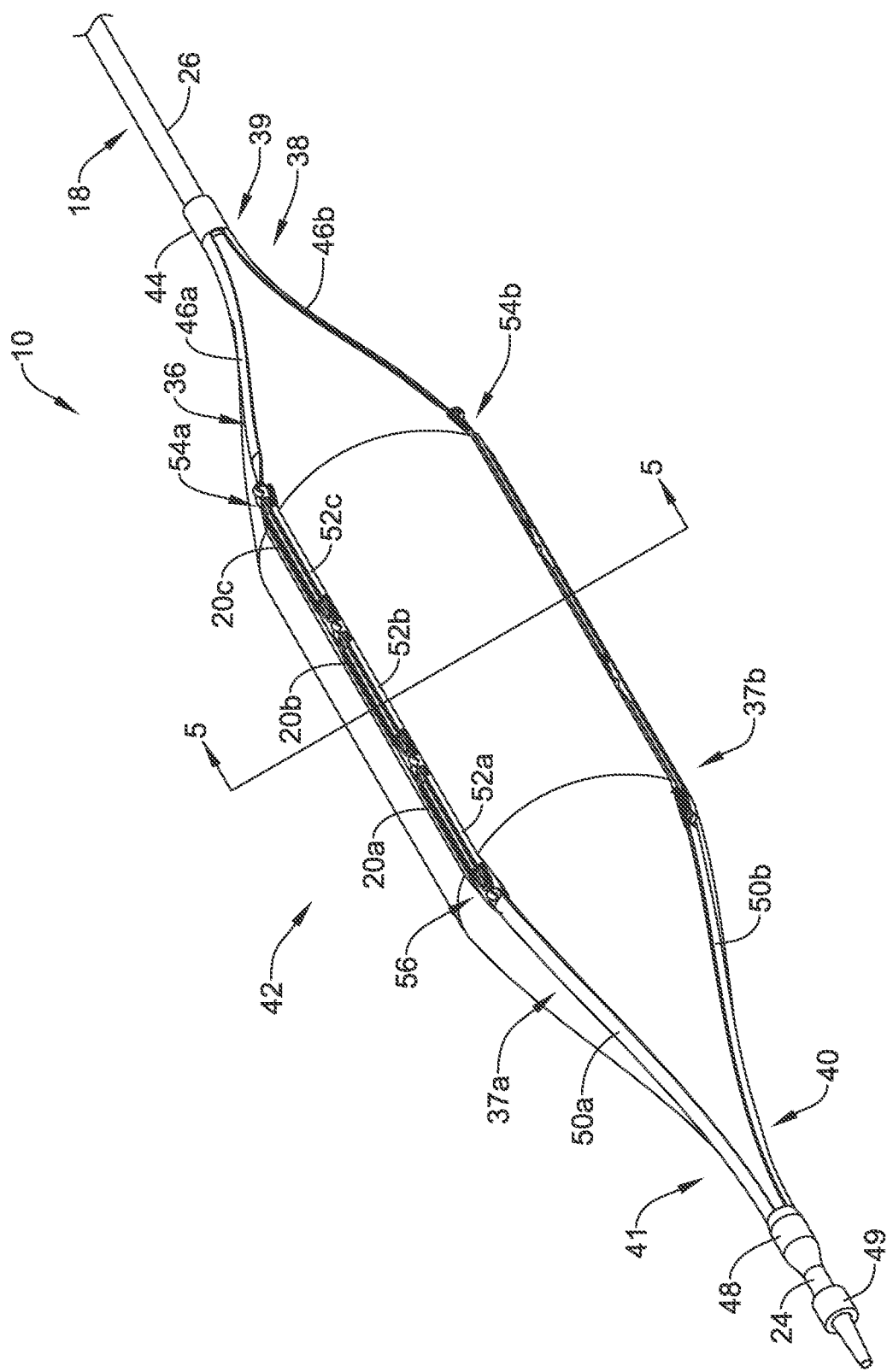
FIG. 2 is a perspective view of an illustrative cutting balloon catheter.
Figure 3:
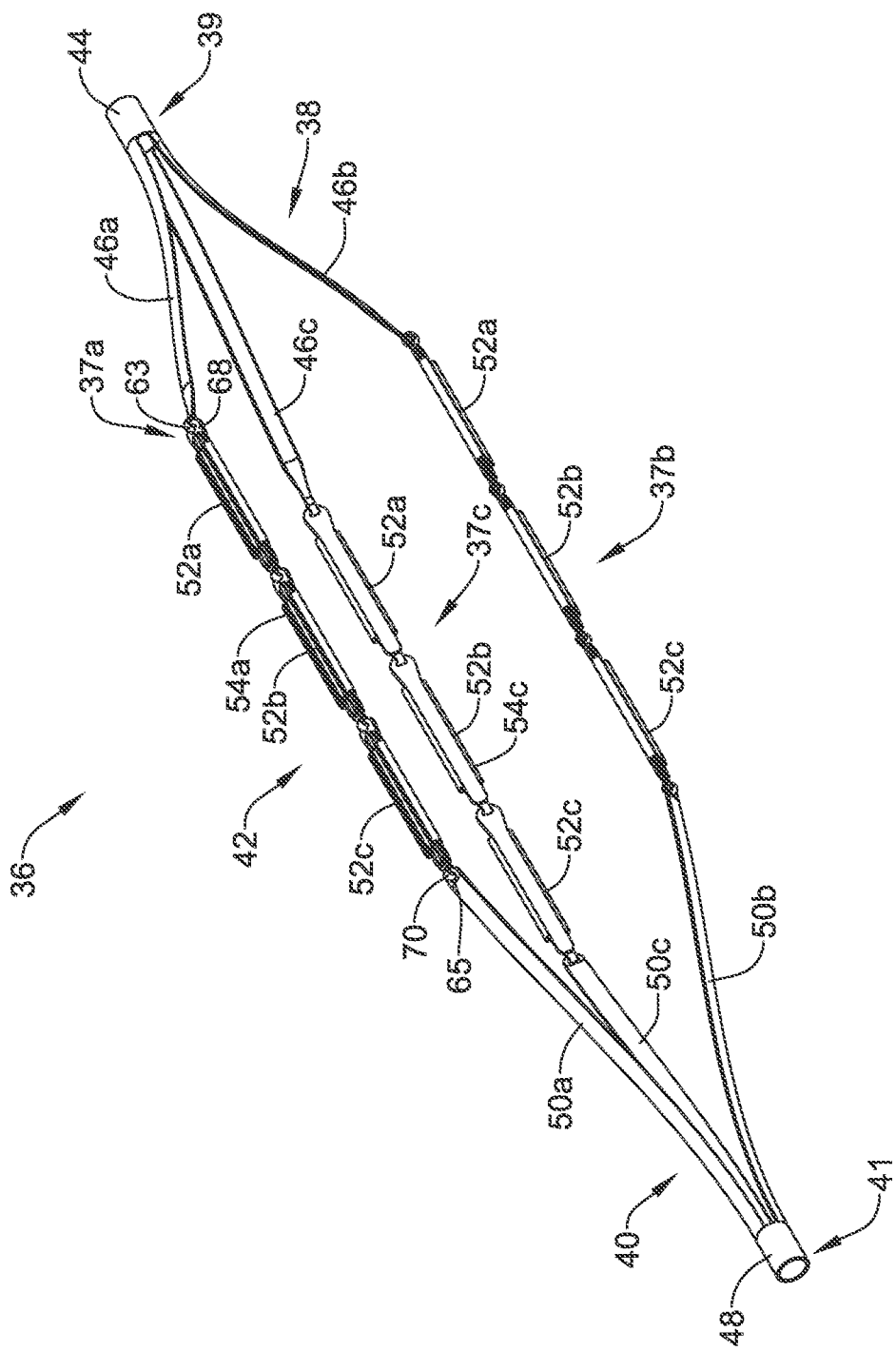
FIG. 3 is a perspective view of an illustrative expandable frame for use with the cutting balloon.

FIG. 2 illustrates a perspective view of the illustrative catheter 10. The one or more cutting members 20 may be mounted relative to the balloon 16 using an expandable frame 36. Referring additionally to FIG. 3 which illustrates a perspective view of the illustrative expandable frame 36, the expandable frame 36 may include a plurality of struts 37a, 37b, 37c (collectively, 37) extending axially along a longitudinal axis of the catheter 10 from a proximal end region 39 to a distal end region 41. While the expandable frame 36 is illustrated as having three struts 37, it is contemplated that the frame 36 may include any number of struts 37 desired, such as, but not limited to, one, two, three, four, or more. In some embodiments, the struts 37 may be configured to be uniformly positioned about a circumference of the balloon 16. For example, the struts 37 may be configured to have an (or approximately) even or equal spacing between adjacent struts 37. Alternatively, the struts 37 may be eccentrically positioned about the circumference of the balloon 16. For example, the struts 37 may have unequal spacing between adjacent struts 37.

The expandable frame 36 may have a proximal section 38, a distal section 40, and an intermediate region 42. The proximal section 38 may be laser cut from a straight hypotube to form a proximal collar 44 with a plurality of tines or arms 46a, 46b, 46c (not shown in FIG. 2) (collectively, 46) extending distally therefrom. Similarly, the distal section 40 may be also be a laser cut from a straight hypotube to form a distal collar 48 with a plurality of tines or arms 50a, 50b, 50c (not shown in FIG. 2) (collectively, 50) extending proximally therefrom. In other instances, the proximal section 38 and/or the distal section 40 may be cut from a flat sheet and rolled into the desired shape. The proximal section 38 and/or the distal section 40 may be formed from spring steel or nitinol and heat set or stress relieved in a collapsed configuration (not explicitly shown). However, other materials may be used, as desired. The proximal section 38 and the distal section 40 of the expandable frame 36 may be moved from the collapsed configuration into the expanded configuration shown in FIG. 2 through expansion of the balloon 16.

The intermediate section 42 may include a plurality of struts 54a, 54b, 54c (not shown in FIG. 2) (collectively, 54) configured to extend between the proximal section 38 and the distal section 40. The proximal section 38 may be coupled, such as pivotably coupled, to the intermediate section 42. Furthermore, the distal section 40 may be coupled, such as pivotably coupled, to the intermediate section 42. In some instances, the proximal section 38 may include one or more hooks 63 configured to be releasably coupled within one or more mating apertures 68 of the intermediate section 42. The reverse configuration is also contemplated in which the proximal section 38 includes one or more apertures configured to receive one or more mating hooks on the intermediate section 42. In some embodiments, the distal section 40 may include one or more apertures 65 configured to be releasably coupled with one or more hooks 70 of the intermediate section 42. The reverse configuration is also contemplated in which the distal section 40 includes one or more hooks configured to be received within one or more mating apertures on the intermediate section 42. The hooks 63, 70 and/or the apertures 65, 68 may allow the links 52 to pivotably couple with the proximal section 38 and/or the distal section 40 which may allow the expandable frame 36 to move between a collapsed generally linear configuration and expanded configuration generally conforming to an outer shape of the balloon 16. For example, the pivotable linkage between the proximal section 38 and the intermediate section 42 as well as the pivotable linkage between the distal section 40 and the intermediate section 42 may allow the intermediate section 42 to extend generally parallel to a longitudinal axis of the balloon 16 while the proximal and distal section 38, 40 extend at a nonparallel angle to the longitudinal axis of the balloon 16.

Each strut 54 may include a plurality of links 52a, 52b, 52c (collectively, 52) with each link 52 carrying a cutting member 20. In some cases, the links 52 may be releasably pivotably coupled to one another, the proximal section 38 and/or the distal section 40. In other embodiments, the struts 54 may form a single link. Alternatively, or additionally, the intermediate section 42 may include a combination of struts 54 having either a single link or a plurality of links.

The expandable frame 36 may be secured to the balloon 16 and/or catheter shaft 18 at one end thereof. For example, the expandable frame 36 may be fixedly secured to the outer tubular member 26 at or adjacent to the proximal collar 44 while the distal collar 48 may be axially slidable about the inner tubular member 24 along a longitudinal axis of the catheter 10. This may allow the expandable frame 36 to lengthen (along the longitudinal axis of the catheter 10) when in the collapsed configuration and shorten when in the expanded configuration. The reverse configuration is also contemplated in which the distal collar 48 is fixedly secured to the inner tubular member 24 while the proximal collar 44 is free to slide axially along the outer tubular member 26. In some cases, both the proximal collar 44 and the distal collar 48 may be fixedly secured to the catheter 10. In other cases, both the proximal collar 44 and the distal collar 48 may be free to slide relative to the catheter 10. It is further contemplated that the expandable frame 36 may be coupled (additionally or alternatively to the proximal and/or distal collars 44, 48) at locations other than the proximal or distal collars 44, 48, as desired.

In some embodiments a ramp or bumper 49 may be provided at a location adjacent to the distal collar 48. The bumper 49 may be structured to prevent the distal collar 48 from catching on a vessel wall (which may result in accidental expansion of the expandable frame 36) while navigating the catheter 10 to the desired treatment location. It is contemplated that the distal collar 48 may butt up against a proximal end of the bumper 49. In other embodiments, the bumper 49 may include a recess configured to receive the distal collar 48 therein.

Figure 4:
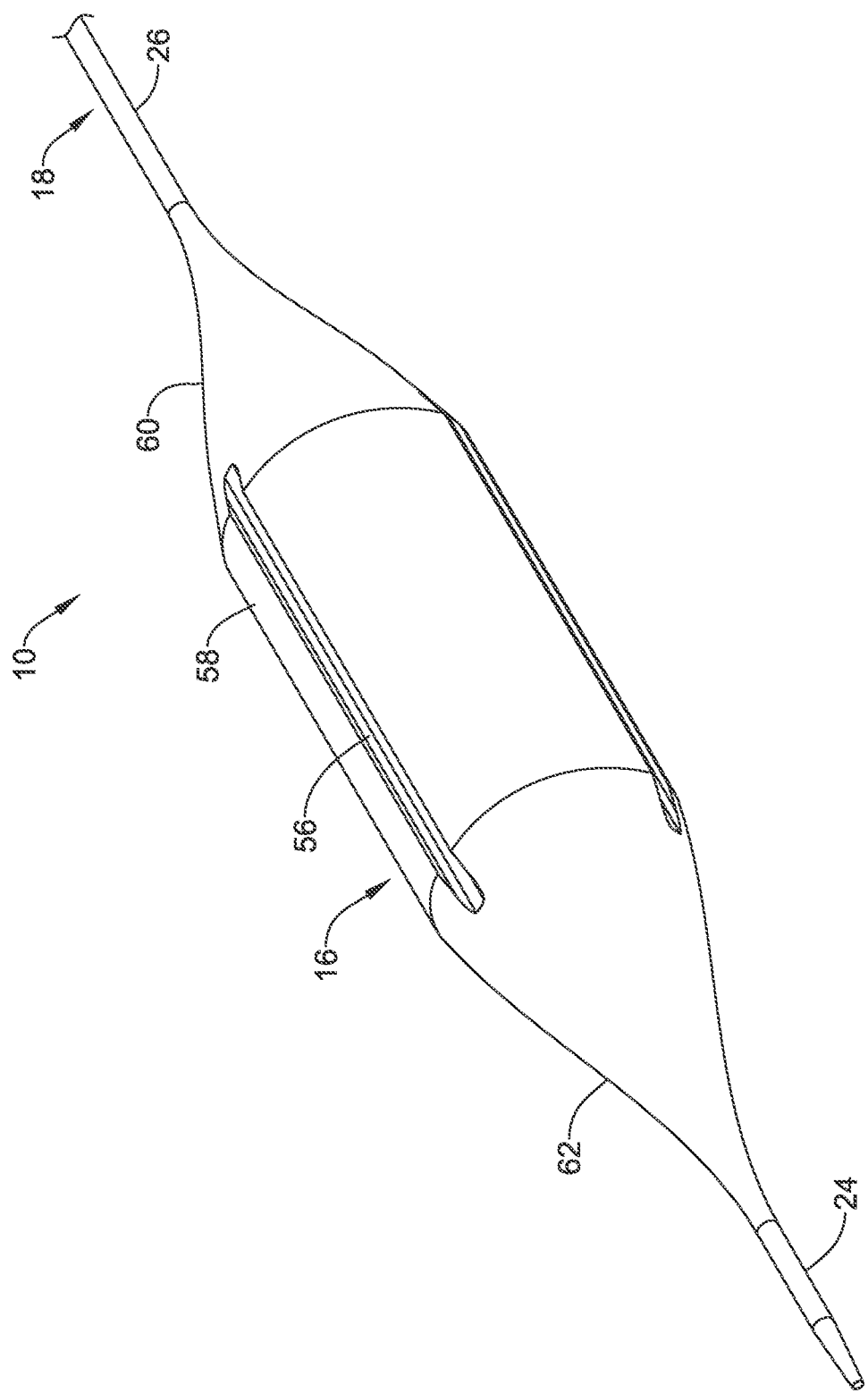
FIG. 4 is another perspective view of an illustrative balloon catheter.

The intermediate section 42 of the expandable frame 36 may be configured to be positioned within recesses or channels 56 formed in an outer surface of the balloon 16. FIG. 4 illustrates a perspective view of the illustrative catheter 10 with the expandable frame 36 removed. The channels 56 are configured to remain when the balloon 16 is expanded. The channels 56 may be substantially parallel to a longitudinal axis of the balloon 16, or the channels may be arranged in other configurations. For example, the channels 56 may be sized and shaped to accommodate at least the intermediate section 42 of the expandable frame 36. If the intermediate section 42 of the expandable frame 36 has a helical or spiral shape, it is contemplated that the channels 56 may also have a helical or spiral shape such that the intermediate section 42 may rest within the channel 56. In some examples, the channels 56 may have a tapered, or dovetail, configuration in which a base of the channel 56 is wider than a top opening into the channel 56 measured between opposite side surfaces of the channel 56. This may allow the frame 36 to be slid longitudinally into the channels 56 while limiting radial movement of the frame 36, such as preventing the frame 36 from being radially removed from the channel 56 in a radial direction. Thus, the radially outwardly facing opening into the channel 56 through which the cutting member 20 extends through may have a width less than the width of the frame 36.

During assembly, the expandable frame 36 may be positioned about the balloon 16 such that the intermediate section 42 (e.g., struts 54) of the expandable frame 36 aligns with the channels 56. Securement of the proximal collar 44 and/or the distal collar 48 may prevent or limit rotational movement of the expandable frame 36 relative to the balloon 16. It is contemplated that once deflated or unexpanded, if the intermediate section 42 of the expandable frame 36 becomes unaligned with the channels 56 as the balloon 16 is expanded, the struts 54 may automatically fall into the grooves 26.

In some embodiments, the expandable frame 36 may help control bulges within the balloon 16 as the balloon 16 is expanded. For example, it is contemplated that the bulges may first occur at or adjacent to the channels 56. Bulges occurring at or adjacent to the channels 56 may provide an additional radially outward extending force on the cutting elements 20 to further score an adjacent lesion. It is contemplated that while bulges may first occur at the channels 56 some bulges may then move towards the region between adjacent struts 37 and/or to proximal or distal cones 60, 62. The configuration of the expandable frame 36 may be selected to control how and where bulges may occur.

In the embodiments illustrated, the balloon 16 may have three channels 56 extending axially along the balloon 16. Any number of channels 56 may be included in the balloon 16. For example, the balloon 16 may include the same number of channels 56 as the frame 36 has struts 37, although this is not required. In some instances, the balloon 16 may include more channels 56 than struts 37 with some channels 56 not occupied by struts 37, or the balloon 16 may include fewer channels 56 than struts 37 with some struts 37 not positioned in channels 56. The channels 56 may be spaced apart in a manner that coincides to or matches the spacing of the struts 37 of the expandable frame 36 such that the struts 37 may be at least partially positioned within the channels 56.

The balloon 16 may include a central body portion 58, the proximal cone 60, and the distal cone 62. The channels 56 may extend from a distal portion of the proximal cone 60, through the body portion 58 to a proximal portion of the distal cone 62. The channel 56 may be sized and shaped to allow the intermediate section 42 of the frame 36 to lie flat on an outer surface of the balloon 16 when the balloon 16 is in the expanded configuration. In some embodiments, the intermediate section 42 may extend proximally or distally beyond the body portion 58. This may allow the proximal section 38 and/or the distal section 40 of the expandable frame 36 to be movably (e.g., pivotably) coupled with the intermediate section 42 without placing a bending stress on any of the proximal section 38, distal section 40 and/or intermediate section 42. It is contemplated that the length of the channels 56 may vary depending on the structure of the frame 36. For example, the channels 56 need not extend an entire length of the body portion 58 or into the proximal and/or distal cones 60, 62.

Figure 5:
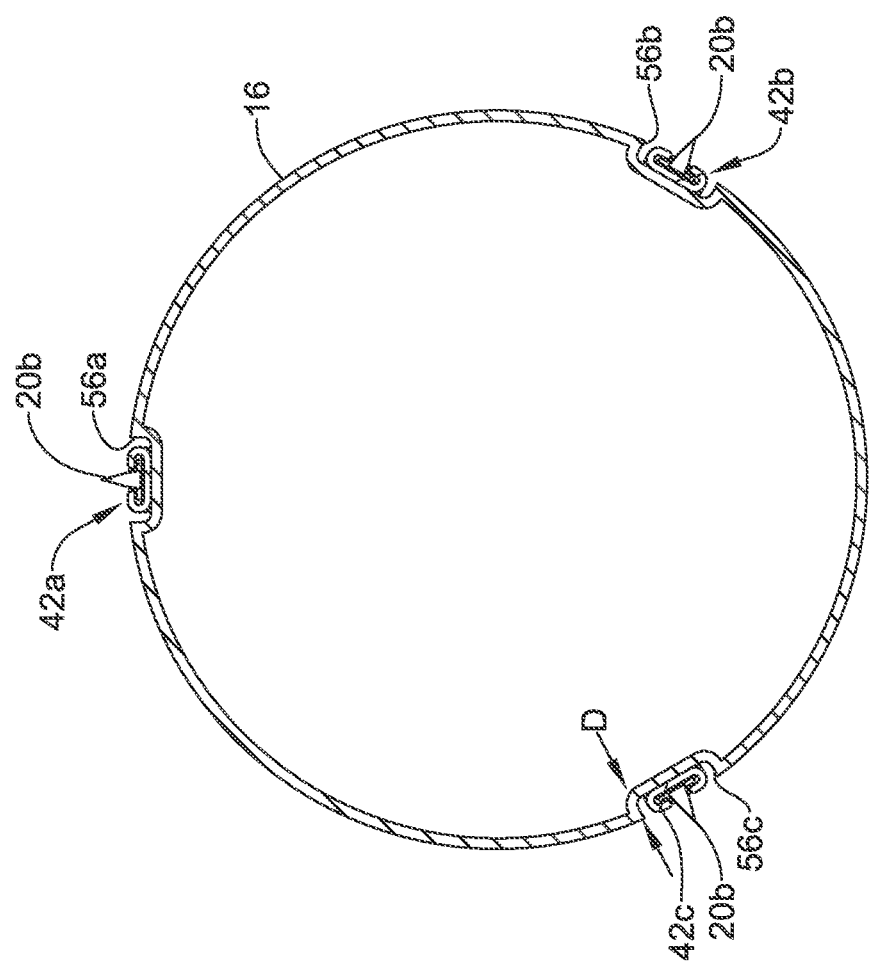
FIG. 5 is a cross-sectional view of the illustrative balloon catheter of FIG. 2 taken at line 2- to of FIG. 2.

FIG. 5 illustrates a cross-sectional view of the illustrative catheter 10 taken at line 5-5 of FIG. 2. The balloon 16 may include three channels 56a, 56b, 56c (collectively, 56) each configured to receive a portion 42a, 42b, 42c of the expandable frame 36. The channels 56 may be sized such that the cutting members 20a, 20b, 20c extend radially beyond the outer diameter (in a region free of channels 56) of the body portion 58 of the balloon 16. For example, the depth D of the channels 56 may be selected such that the sharpened tip or edge of the cutting members 20 extend radially outward beyond a maximum outer diameter of the balloon 16. This may allow the cutting members 20 to penetrate a lesion when the balloon 16 is inflated adjacent to the lesion.

In some embodiments, the channels 56 may be molded into the balloon 16 such that the balloon 16 has a uniform wall thickness in both the channels 56 and the regions free from the channels 56. However, it is contemplated that the channels 56 may be formed using other methods, such as removal of material in the wall of the balloon 16 to form the channels 56, as desired.

Figure 6:
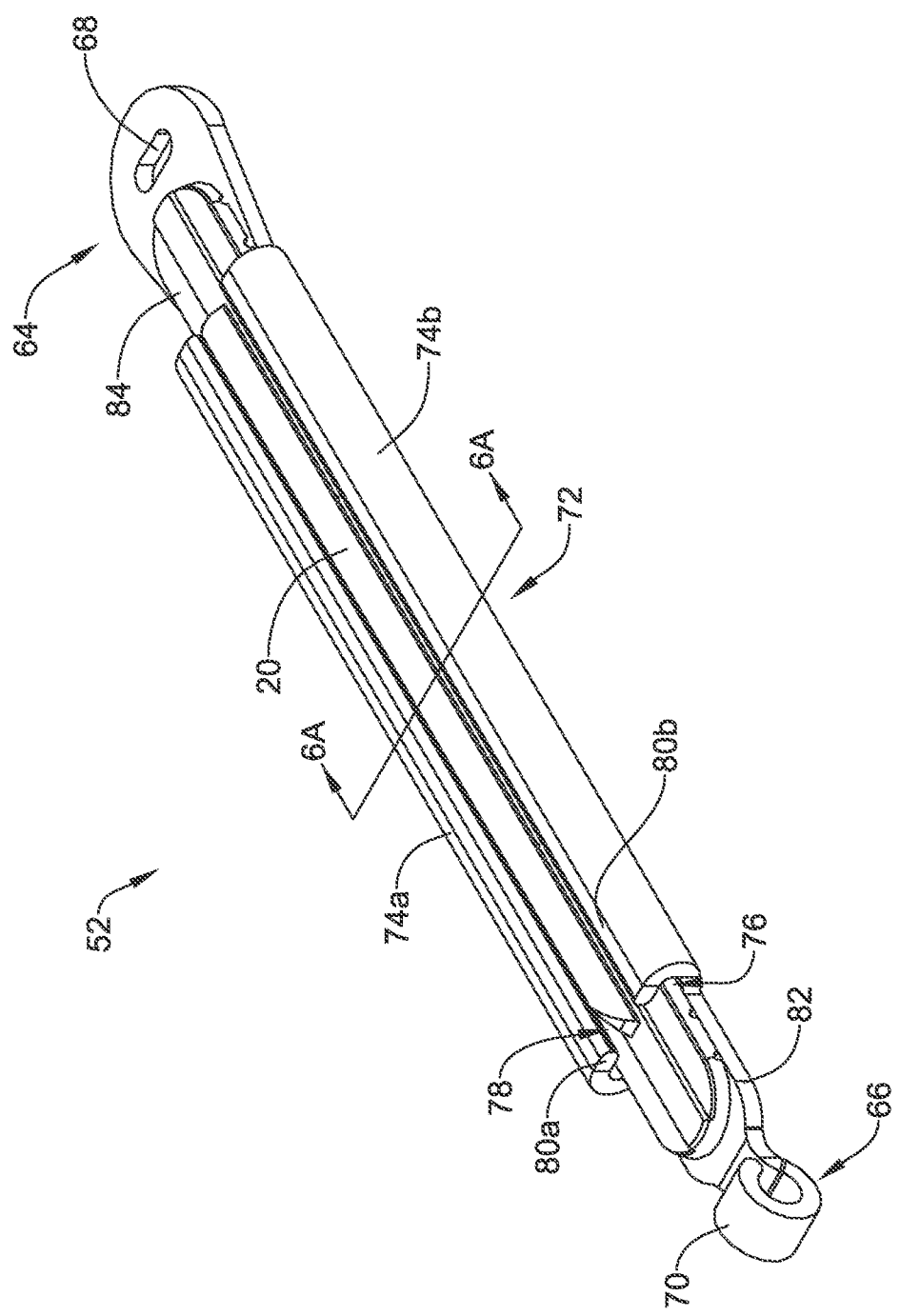
FIG. 6 is a perspective view of an illustrative link for use in expandable frame of FIG. 3.

FIG. 6 is a perspective view of an illustrative cartridge or link 52 forming a portion of the intermediate section 42 of the expandable frame 36. The link 52 may include a first or proximal end region 64, a second or distal end region 66, and an intermediate region 72. In some embodiments, the links 52 may be cut and bent from a flat sheet of metal. The proximal end region 64 of the link 52 may include an aperture 68 configured to receive a loop or hook on adjacent structure. In some cases, the adjacent structure may be the proximal section 38 of the expandable frame 36, the distal section 40 of the expandable frame 36, and/or an adjacent link 52. The distal end region 66 of the link 52 may include a loop or hook 70 configured to engage an aperture on an adjacent structure. In some cases, the adjacent structure may be the proximal section 38 of the expandable frame 36, the distal section 40 of the expandable frame 36, and/or an adjacent link 52. For example, the link 52 may be configured to engage an adjacent link to form a chain of links 52 having a plurality of pivotable hinge points between adjacent links 52, as shown in the intermediate section 42 of the expandable frame 36 in FIGS. 2 and 3. It is further contemplated that other coupling mechanisms besides hooks and apertures may be used to releasably couple and/or pivotably couple adjacent links and/or the intermediate section 42 to the proximal and/or distal section 38, 40.

Figure 6A:
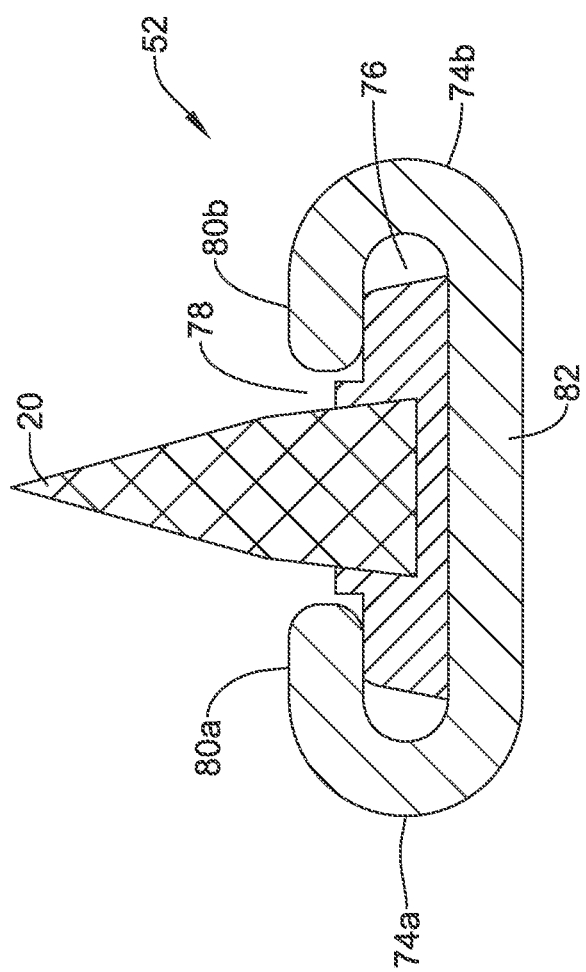
FIG. 6A is a cross-sectional view of the illustrative link of FIG. 6 taken at line 6A-6A.

Referring additionally to FIG. 6A, which illustrates a cross-sectional view of the illustrative link of FIG. 6 taken at line 6A-6A, the intermediate region 72 of the link 52 may include a pair of U-shaped arms 74a, 74b (collectively, 74). The U-shaped arms 74 in combination with the bottom wall 82 of the link 52 may define an axially extending channel 76 extending generally parallel to a longitudinal axis of the link 52. The channel 76 may be configured to slidably receive a cutting member 20 therein. A gap or opening 78 may be defined between a top portion 80a, 80b (collectively, 80) of the respective arms 74. The opening 78 may allow the cutting member 20 to extend beyond the top portion 80 of the arms 74 in a direction generally perpendicular to the longitudinal axis of the link 52. As described herein, when the cutting member 20 is mounted relative to the balloon 16, the cutting member 20 may be configured to extend radially outward beyond the greatest extent of the outer diameter of the balloon 16.

In some instances, the cutting member 20 may be secured within the channel 76 using a number of different techniques including, for example, adhesives, soldering, brazing, welding, etc. In other instances, the arms 74 may be squeezed or crimped onto the cutting member 20 to create a mechanical interlock or friction fit between the arms 74 and the cutting member 20. It is further contemplated that the arms 74 may include a downward extending tab or lip configured to engage a groove within a mounting pad 84 of the cutting member 20, for example. As shown in FIG. 6A, a surface of the arms 74 may press against or contact a surface of the cutting member 20 to retain the cutting member 20 in the channel 76.

As described herein, any number of links 52 may be coupled together to provide a cutting member system that will create a long cutting plane. To couple the links 52, a hook 70 of a first link 52 may be looped through an aperture 68 of a second or adjacent link 52. Once the hook 70 is engaged with the aperture 68, the hook 70 may be mechanically deformed to secure the first link 52 relative to the second link 52. In some embodiments, it is contemplated that the hook 70 may have a generally straight configuration, or slightly curved configuration, prior to assembly with another link 52, proximal section 38 of the frame 36, and/or distal section 40 of the frame 36. In such an instance, the hook 70 may be mechanically deformed into the looped configuration illustrated in FIG. 6 after assembly with a corresponding aperture 65, 68.

It is contemplated that as any number of links 52 may be coupled together, the expandable frame 36 may be customizable for a variety of lengths of balloons 16. It is further contemplated that as the cutting elements 20 are not secured directly to the cutting balloon 16, bulges or other deformations in the balloon 16, as the balloon 16 is being expanded, may not impact the securement and/or positioning of the cutting elements 20. For example, as the expandable frame 36 is coupled to the balloon 16 at one end of the frame 36 (e.g., proximal collar 44 or distal collar 48), the opposing end and/or the intermediate struts 37 may be free to shift axially about the longitudinal axis and/or circumferentially about the balloon 16 as necessary.

In some embodiments it may be desirable for the cutting element 20 to extend radially beyond an outer diameter of the balloon 16 to a similar extent or degree as if it were mounted directly to the outer surface of the balloon 16 (for example, without the link 52). In some embodiments, the channel 56 may have a depth D (see, for example, FIG. 5) that is approximately equal to a thickness of the bottom wall 82 of the link 52. For example, the channel may have a depth that is in the range of 0.002 to about 0.006 inches (about 0.051 mm to 0.152 mm) or about 0.004 inches (0.102 mm).

Figure 7:
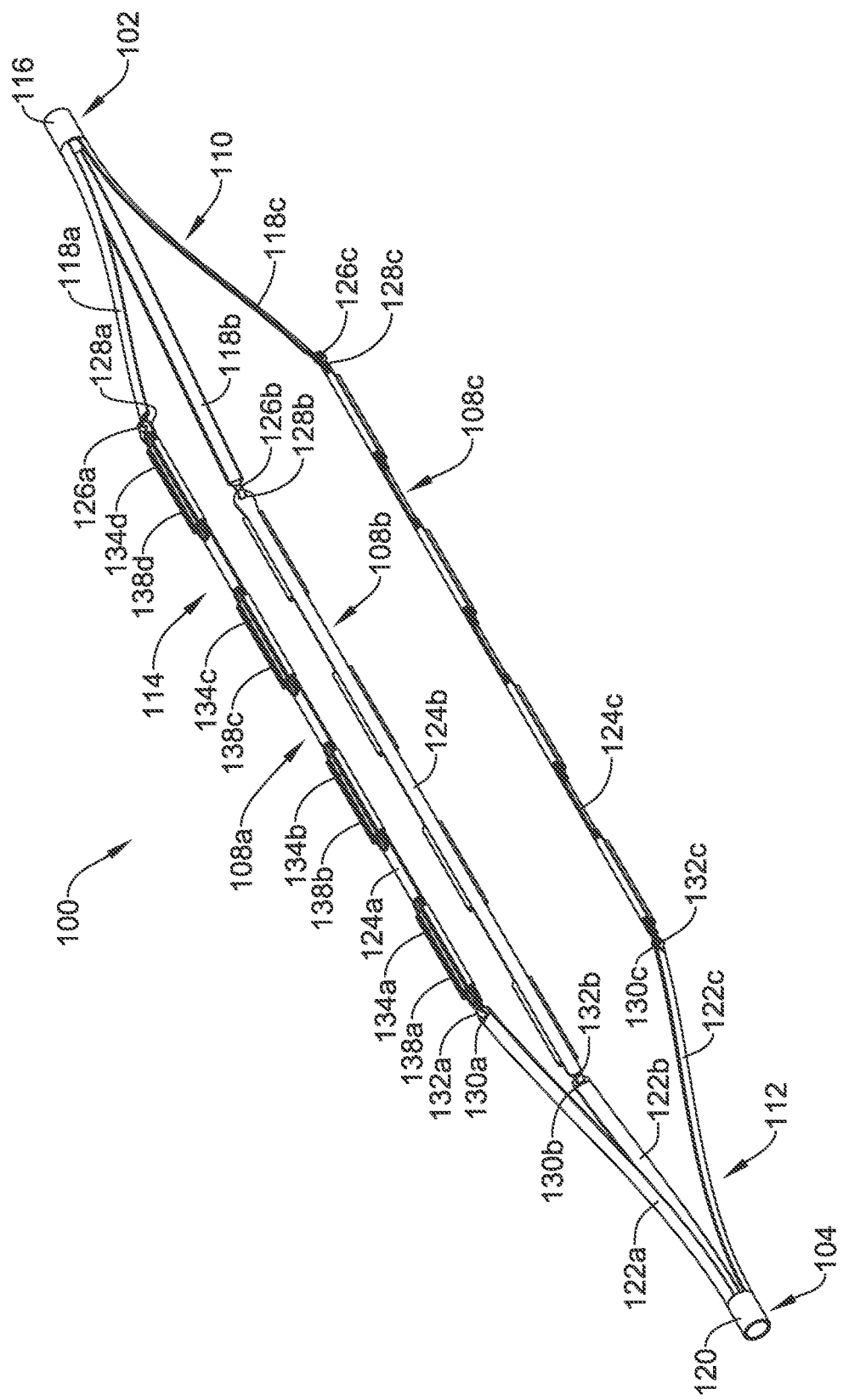
FIG. 7 is a perspective view of another illustrative expandable frame for use with the cutting balloon.

FIG. 7 is a perspective view of another illustrative expandable frame 100 for mounting one or more cutting members relative to an expandable balloon. The expandable frame 100 may include a plurality of struts 108a, 108b, 108c (collectively, 108) extending axially along a longitudinal axis of the frame 100 from a proximal end region 102 to a distal end region 104. While the expandable frame 100 is illustrated as having three struts 108, it is contemplated that the frame 100 may include any number of struts 108 desired, such as, but not limited to, one, two, three, four, or more. In some embodiments the struts 108 may be configured to be uniformly positioned about a circumference of a balloon. For example, the struts 108 may be configured to have an (or approximately) even or equal spacing between adjacent struts 108. Alternatively, the struts 108 may be eccentrically positioned about the circumference of the balloon. For example, the struts 108 may have unequal spacing between adjacent struts 108.

The expandable frame 100 may have a proximal section 110, a distal section 112, and an intermediate region 114. The proximal section 110 may be laser cut from a straight hypotube to form a proximal collar 116 with a plurality of tines or arms 118a, 118b, 118c (collectively, 118) extending distally therefrom. Similarly, the distal section 112 may be also be a laser cut from a straight hypotube to form a distal collar 120 with a plurality of tines or arms 122a, 122b, 122c (collectively, 122) extending proximally therefrom. In other instances, the proximal section 110 and/or the distal section 112 may be cut from a flat sheet and rolled into the desired shape. The proximal section 110 and/or the distal section 112 may be formed from spring steel or nitinol and heat set or stress relieved in a collapsed configuration (not explicitly shown). However, other materials may be used, as desired. The proximal section 110 and the distal section 112 of the expandable frame 100 may be moved from the collapsed configuration into the expanded configuration shown in FIG. 2 through expansion of the balloon 16.

The intermediate section 114 may include a plurality of struts 124a, 124b, 124c (collectively, 124) configured to extend between the proximal section 110 and the distal section 112. In some instances, the proximal section 110 may include a hook or loop 126a, 126b, 126c (collectively, 126) adjacent to a distal end of the tines 118. The hooks 126 may be configured to be releasably and pivotably coupled within one or more mating apertures 128a, 128b, 128c (collectively, 128) formed in a proximal end region of the struts 124 of the intermediate section 114. The reverse configuration is also contemplated in which the proximal section 110 includes one or more apertures configured to receive one or more mating hooks on the intermediate section 114. In some embodiments, the distal section 112 may include an aperture 130a, 130b, 130c (collectively, 130) adjacent to a proximal end of the tines 122. The apertures 130 may be configured to be releasably and pivotably coupled with one or more hooks or loops 132a, 132b, 132c (collectively, 132) formed in a distal end region of the struts 124 of the intermediate section 114. The reverse configuration is also contemplated in which the distal section 112 includes one or more hooks configured to be received within one or more mating apertures on the intermediate section 114. The hooks 126, 132 and/or the apertures 128, 130 may be similar in form and function to those described with respect to FIGS. 3 and 6. The hooks 126, 132 and/or the apertures 128, 130 may allow the intermediate section 114 to pivotably couple with the proximal section 110 and/or the distal section 112 which may allow the expandable frame 100 to move between a collapsed generally linear configuration and expanded configuration generally conforming to an outer shape of the balloon. For example, the pivotable linkage between the proximal section 110 and the intermediate section 114 as well as the pivotable linkage between the distal section 112 and the intermediate section 114 may allow the intermediate section 114 to extend generally parallel to a longitudinal axis of the balloon while the proximal and distal section 110, 112 extend at a nonparallel angle to the longitudinal axis of the balloon.

Figure 8:
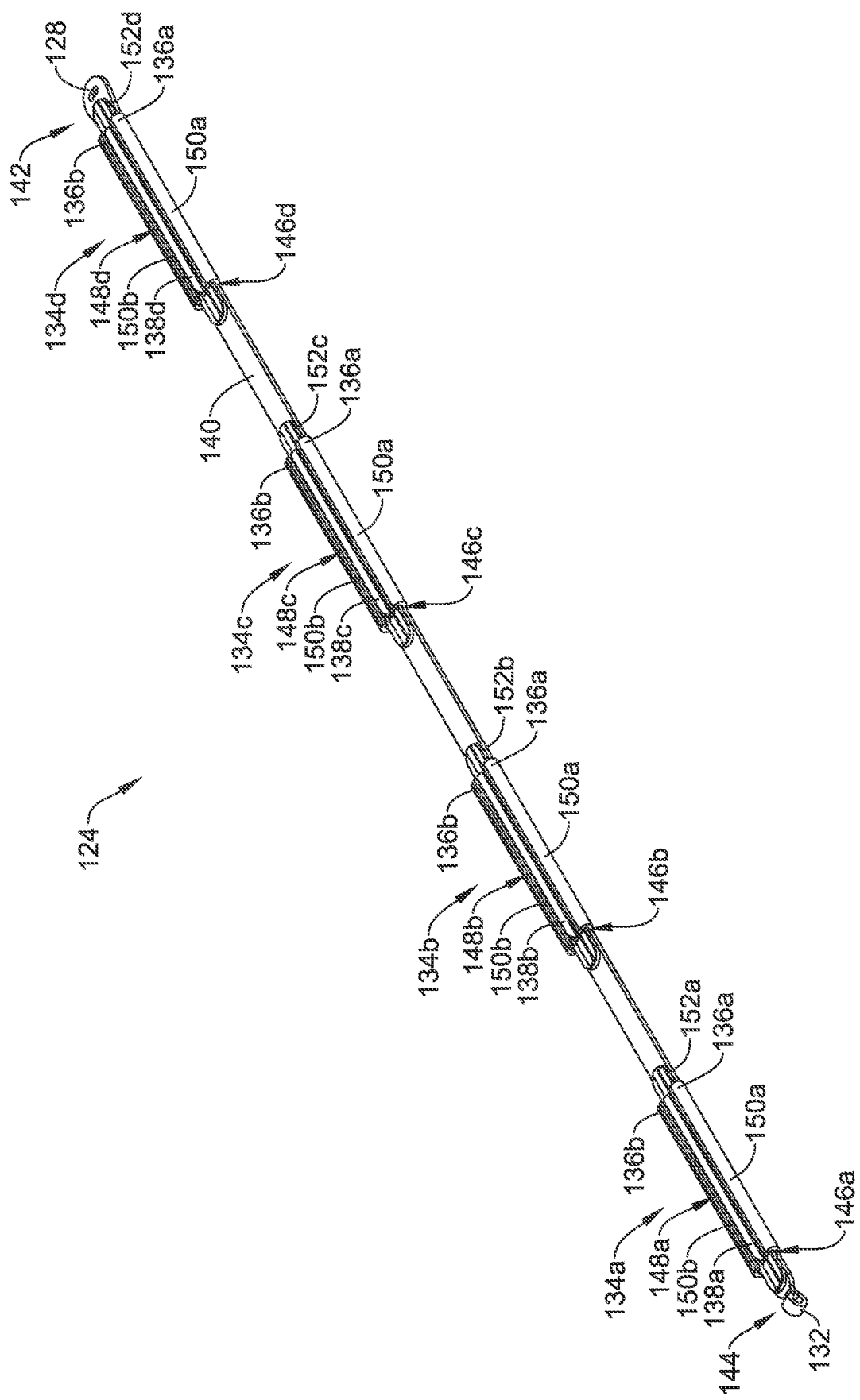
FIG. 8 is a perspective view of an illustrative strut of the expandable frame of FIG. 7.

Each strut 124 may include a plurality of mounting modules 134a, 134b, 134c, 134d (collectively, 134) configured to secure a cutting element or member 138a, 138b, 138c, 138d (collectively, 138) to the expandable frame 100. FIG. 8 illustrates a perspective view of an illustrative strut 124 of the intermediate section 114. A base member 140 may extend from a proximal end 142 to a distal end 144 of the strut 124. The aperture 128 for receiving a hook 126 of the proximal section 110 of the expandable basket 100 may be formed in the proximal end region 142 of the strut 124. The hook 132 for coupling to an aperture of the distal section 112 of the expandable basket 100 may be formed in the distal end region 144 of the strut 124. In some embodiments the configuration may be reversed in which the aperture 128 is formed in the distal end region 144 of the strut 124 and the hook 132 is formed in the proximal end region 142 of the strut 124.

It is contemplated that the mounting modules 134 may be formed as a unitary or monolithic structure with the base member 140. For example, the strut 124 may be stamped or cut from a flat sheet of metal and bent to form the illustrated structure. In other embodiments, the mounting modules 134 may be formed as separate components that are secured to the base member 140. Each of the mounting modules 134 may include a pair of U-shaped arms 136a, 136b (collectively, 136). The U-shaped arms 136 in combination with the base member of the strut 124 may define an axially extending channel 146a, 146b, 146c, 146d (collectively, 146) extending generally parallel to a longitudinal axis of the strut 124. Each channel 146 may be configured to slidably receive a respective cutting member 138 therein along the longitudinal axis. A gap or opening 148a, 148b, 148c, 148d (collectively, 148) may be defined between a top portion 150a, 150b (collectively, 150) of the respective arms 136. The opening 148 may allow the cutting member 138 to extend beyond the top portion 150 of the arms 136 in a direction generally perpendicular to the longitudinal axis of the strut 124. As described herein, when the cutting member 138 is mounted relative to the balloon, a sharpened tip or edge of the cutting member 138 may be configured to extend radially outward beyond the largest extent of the outer diameter of the balloon.

In some instances, the cutting member 138 be secured within the channel 146 using a number of different techniques including, for example, adhesives, soldering, brazing, welding, etc. In other instances, the arms 136 may be squeezed or crimped onto the cutting member 138 to create a mechanical interlock or friction fit between the arms 136 and the cutting member 138. It is further contemplated that the arms 136 may include a downward extending tab or lip configured to engage a groove within a mounting pad 152a, 152b, 152c, 152d (collectively, 152) of the cutting member 138.

The expandable frame 100 may be secured to a balloon and/or a catheter shaft at one end thereof. For example, the expandable frame 100 may be secured to the catheter shaft at or adjacent to the proximal collar 116 while the distal collar 120 may be axially slidable about the catheter shaft along a longitudinal axis of the catheter. This may allow the expandable frame 100 to lengthen (along the longitudinal axis of the catheter) when in the collapsed configuration and shorten when in the expanded configuration. The reverse configuration is also contemplated in which the distal collar 120 is coupled to the catheter shaft while the proximal collar 116 is free to slide axially along the catheter shaft. In some cases, both the proximal collar 116 and the distal collar 120 may be coupled to the catheter. It is further contemplated that the expandable frame 100 may be coupled (additionally or alternatively to the proximal and/or distal collars 116, 120) at locations other than the proximal or distal collars 116, 120, as desired.

The strut 124 may include any number of mounting modules 134 to provide a cutting member system that will create a long cutting plane. For example, the strut 124 may include one, two, three, four or more mounting modules 134 to provide any length of cutting plane desired. It is further contemplated that as the cutting elements 138 are not secured directly to the balloon, bulges or other deformations in the balloon, as the balloon is being expanded, may not impact the securement and/or positioning of the cutting elements 138. For example, as the expandable frame 100 is coupled to the balloon at one end of the frame 100 (e.g., proximal collar 116 or distal collar 120), the opposing end and/or the intermediate struts 124 may be free to shift axially about the longitudinal axis and/or circumferentially about the balloon as necessary.

The intermediate section 114 of the expandable frame 100 may be configured to be positioned within recesses or channels formed in the balloon in a similar manner to that described herein. In some embodiments it may be desirable for the cutting element 138 to extend radially beyond an outer diameter of the balloon to a similar extent or degree as if it were mounted directly to the outer surface of the balloon 16 (for example, without the strut 124).

Figure 9:
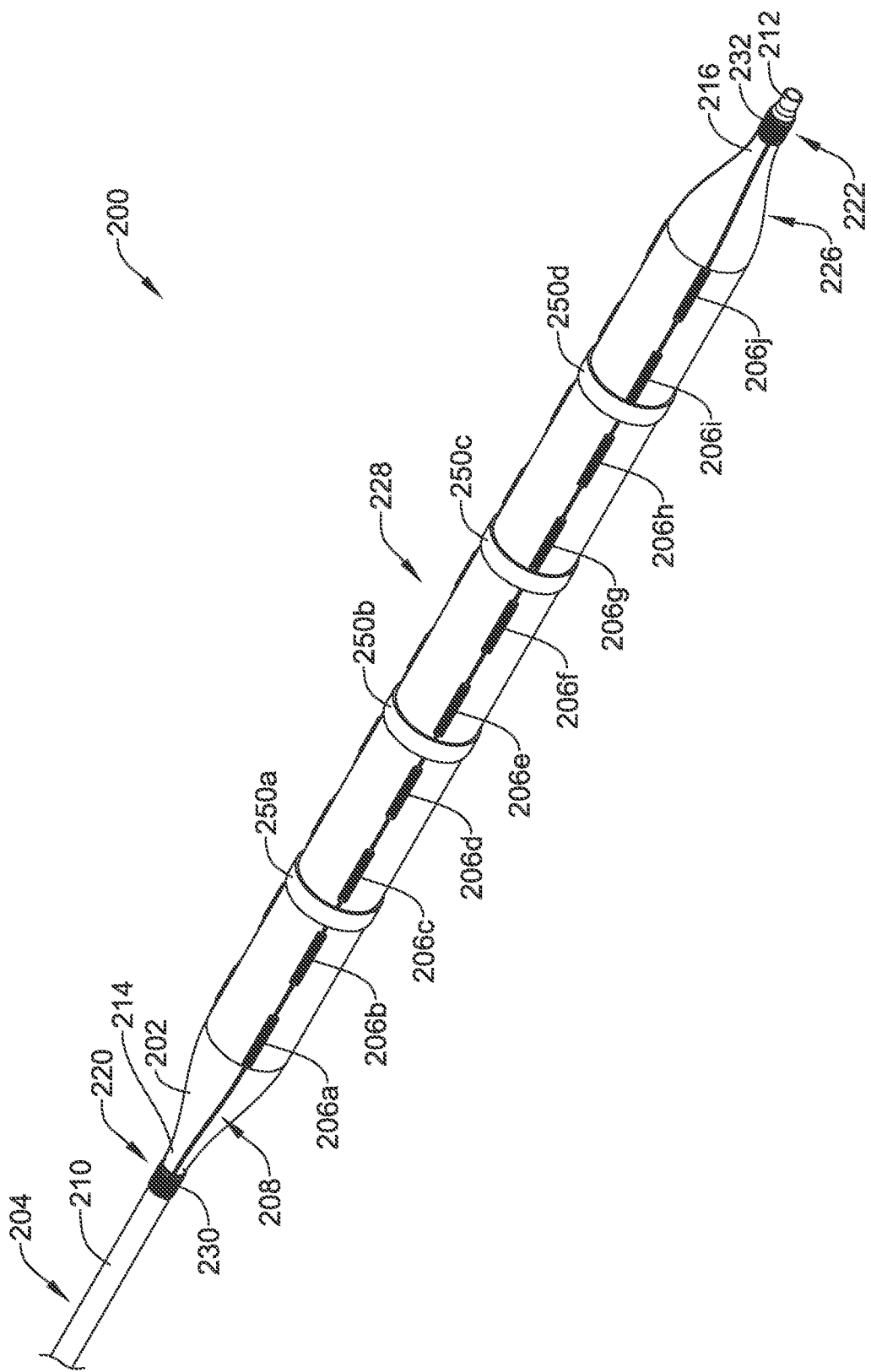
FIG. 9 is a perspective view of another illustrative cutting balloon catheter.

FIG. 9 is a perspective view of another illustrative catheter 200. The catheter 200 may include a balloon 202 coupled to a catheter shaft 204. One or more cutting members or blades 206a-j (collectively, 206) may be mounted on the balloon 202. In some cases, the one or more cutting members 206 may be mounted on an expandable frame or basket 208 which, in turn, may be coupled to the balloon 202 and/or catheter shaft 204. In general, the catheter 200 may be advanced over a guidewire (not explicitly shown), through the vasculature, to a target area. Once positioned at the target location in the vasculature, the balloon 202 can be inflated to exert a radially outward force on a lesion, as the cutting members 206 engage the lesion. Thus, the cutting members 206 may cut or score the lesion to facilitate enlarging the lumen proximate the lesion. The target area may be within any suitable peripheral or cardiac vessel lumen location.

The catheter 200 and/or balloon 202 may be sized for use in critical limb ischemia with very small vessels (e.g., having a diameter in the range of about 2-3 mm). The balloon 202 may have a length in the range of about 60 to 140 mm, about 80 to 120 mm, or about 100 mm, for example. In some instances, the inflated balloon 202 may have an outer diameter in the range of about 1 to 5 mm, about 2 to 4 mm or about 3 mm, for example.

The cutting members 206 may vary in number, position, and arrangement about the balloon 202. For example, the catheter 200 may include one, two, three, four, five, six, or more cutting members 206 that are disposed at any position along the balloon 202 and in a regular, irregular, or any other suitable pattern. For example, in some embodiments the balloon 202 may include a plurality of cutting members 206 longitudinally arranged symmetrically around the circumference of the balloon 202.

The cutting members 206 may be made from any suitable material such as a metal, metal alloy, polymer, metal-polymer composite, and the like, or any other suitable material. For example, cutting members 206 may be made from stainless steel, titanium, nickel-titanium alloys, tantalum, iron-cobalt-nickel alloys, or other metallic materials in some instances.

The balloon 202 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyetherester, polyester, polyamide, elastomeric polyamides, polyether block amide (PEBA), as well as other suitable materials, or mixtures, combinations, copolymers thereof, polymer/metal composites, and the like. In some instances, the balloon 202 may include a single layer of material, whereas in other instances the balloon 202 may be of a multi-layer construction, including a plurality of layers of materials. For instance, the balloon 202 may be formed as a co-extrusion or tri-layer extrusion in some instances.

The balloon 202 may be configured so that the balloon 202 includes one or more "wings" or wing-shaped regions when the balloon 202 is deflated. In some instances, the wings may be configured so that the cutting members 206 can be positioned at the inward-most positions of the deflated balloon 202, with the wings of the balloon folds positioned between adjacent cutting members 206. This arrangement may reduce the exposure of the cutting members 206 to the blood vessel during delivery of the balloon 202 to the lesion.

The shaft 204 may be a catheter shaft, similar to typical catheter shafts. For example, the catheter shaft 204 may include an outer tubular member 210 and an inner tubular member 212 extending through at least a portion of the outer tubular member 210. The tubular members 212, 210 may be manufactured from a number of different materials. For example, the tubular members 212, 210 may be made of metals, metal alloys, polymers, metal-polymer composites or any other suitable materials.

The tubular members 212, 210 may be arranged in any appropriate way. For example, in some embodiments the inner tubular member 212 can be disposed coaxially within the outer tubular member 210. According to these embodiments, the inner and outer tubular members 212, 210 may or may not be secured to one another along the general longitudinal axis of the catheter shaft 204. Alternatively, the inner tubular member 212 may follow the inner wall or otherwise be disposed adjacent the inner wall of the outer tubular member 210. In other embodiments, the tubular members 212, 210 may be arranged in another desired fashion.

The inner tubular member 212 may include an inner lumen (not explicitly shown). In at least some embodiments, the inner lumen is a guidewire lumen for receiving a guidewire therethrough. Accordingly, the catheter 200 can be advanced over the guidewire to the desired location. The guidewire lumen may extend along essentially the entire length of the catheter shaft 204 such that catheter 200 resembles traditional "over-the-wire" catheters. Alternatively, the guidewire lumen may extend along only a portion of the catheter shaft 204 such that the catheter 200 resembles "single-operator-exchange" or "rapid-exchange" catheters.

The catheter shaft 204 may also include an inflation lumen (not explicitly shown) that may be used, for example, to transport inflation media to and from the balloon 202 to selectively inflate and/or deflate the balloon 202. The location and position of the inflation lumen may vary, depending on the configuration of the tubular members 212, 210. For example, when the outer tubular member 210 surrounds the inner tubular member 212, the inflation lumen may be defined within the space between the tubular members 212, 210. In embodiments in which the outer tubular member 210 is disposed alongside the inner tubular member 212, then the inflation lumen may be the lumen of the outer tubular member 210.

The balloon 202 may be coupled to the catheter shaft 204 in any of a number of suitable ways. For example, the balloon 202 may be adhesively or thermally bonded to the catheter shaft 204. In some embodiments, a proximal waist 214 of the balloon 202 may be bonded to the catheter shaft 204, for example, bonded to the distal end of the outer tubular member 210, and a distal waist 216 of the balloon 202 may be bonded to the catheter shaft 204, for example, bonded to the distal end of the inner tubular member 212. The exact bonding positions, however, may vary.

Figure 10:
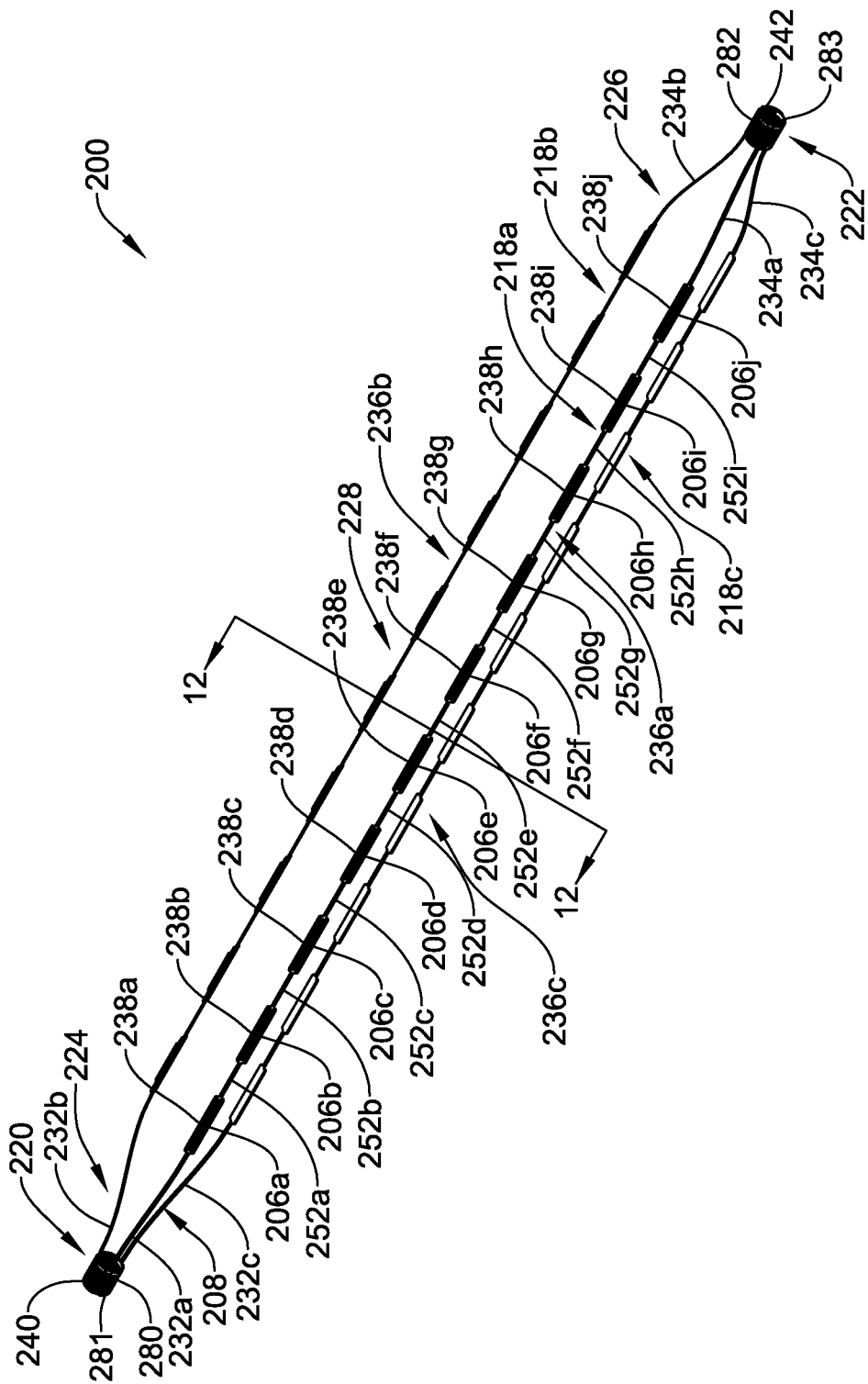
FIG. 10 is a perspective view of another illustrative expandable frame for use with the cutting balloon catheter.

The one or more cutting members 206 may be mounted relative to the balloon 202 using an expandable frame 208. While not explicitly shown, the balloon 202 may include channels similar in form and function to the channels 56 described herein. Referring additionally to FIG. 10 which illustrates a perspective view of the illustrative expandable frame 208, the expandable frame 208 may include a plurality of struts 218a, 218b, 218c (collectively, 218) extending axially along a longitudinal axis of the catheter 200 from a proximal end region 220 to a distal end region 222. While the expandable frame 208 is illustrated as having three struts 218, it is contemplated that the frame 208 may include any number of struts 218 desired, such as, but not limited to, one, two, three, four, or more. In some embodiments, the struts 218 may be configured to be uniformly positioned about a circumference of the balloon 202. For example, the struts 218 may be configured to have an (or approximately) even or equal spacing between adjacent struts 218. Alternatively, the struts 218 may be eccentrically positioned about the circumference of the balloon 202. For example, the struts 218 may have unequal spacing between adjacent struts 218.

The expandable frame 208 may have a proximal section 224, a distal section 226, and an intermediate section 228. The expandable frame 208 may be laser cut from a straight metallic tube (e.g., a hypotube) to form a proximal collar 281, a distal collar 283, and the plurality of struts 218 therebetween. In other instances, the proximal section 224, the distal section 226, and/or intermediate section 228 may be cut from a flat sheet and rolled into the desired shape. In yet other embodiments, the proximal collar 281, distal collar 283 and/or struts 218 may be individually formed from a variety of methods and subsequently coupled together. The proximal section 224 and/or the distal section 226 may be formed from spring steel or nitinol and heat set or stress relieved in a collapsed configuration (not explicitly shown). However, other materials may be used, as desired. The proximal section 224 and the distal section 226 of the expandable frame 208 may be moved from the collapsed configuration into the expanded configuration shown in FIG. 9 through inflation and thus radial expansion of the balloon 202.

Each strut 218 of the expandable frame 208 may include a proximal end region 232a, 232b, 232c (collectively, 232), a distal end region 234a, 234b, 234c (collectively, 234), and an intermediate region 236a, 236b, 236c (collectively, 236) disposed therebetween. As described herein, the struts 218 may be individually cut from a flat sheet or cut from a straight metallic tube (e.g., a hypotube), as desired. In some embodiments, the struts 218 may be formed as a monolithic structure. The proximal end regions 232 and/or the distal end regions 234 may be formed from spring steel or nitinol and heat set or stress relieved in a collapsed configuration (not explicitly shown). However, other materials may be used, as desired.

In some cases, the proximal end regions 232 and/or the distal end regions 234 may be pivotably coupled with the intermediate regions 236. For example, the proximal end regions 232 and/or the distal end regions 234 may bend, flex, and/or pivot relative to the intermediate regions 236 such that the expandable frame 208 may move between a collapsed generally linear configuration and an expanded configuration generally conforming to an outer shape of the balloon 202. For example, the pivotable linkage between the proximal end regions 232 and the intermediate regions 236 as well as the pivotable linkage between the distal end regions 234 and the intermediate section 236 may allow the intermediate section 236 to extend generally parallel to a longitudinal axis of the balloon 202 while the proximal and distal end regions 232, 234 extend at a nonparallel angle to the longitudinal axis of the balloon 202 for at least a portion of their respective lengths.

Each strut 218 may include a plurality of links or mounting modules 238a-j (collectively 238) with each mounting module carrying a cutting member 206. While each strut 218 is illustrated as including ten mounting modules 238, it is contemplated that the struts 218 may include fewer than ten or more than ten mounting modules 238 to form a cutting member system having the desired cutting length. In some cases, the mounting modules 238 may be pivotably coupled to one another, the proximal end region 232, and/or the distal end region 234. For instance, the mounting modules 238 may be separate structures linked or coupled together, or the mounting modules 238 may be formed as a single monolithic or unitary structure with living hinges. Alternatively, or additionally, the intermediate region 236 may include a combination of struts 218 having either a unitary structure including a plurality of mounting modules 238 or a plurality of coupled individual mounting modules 238.

Figure 11:
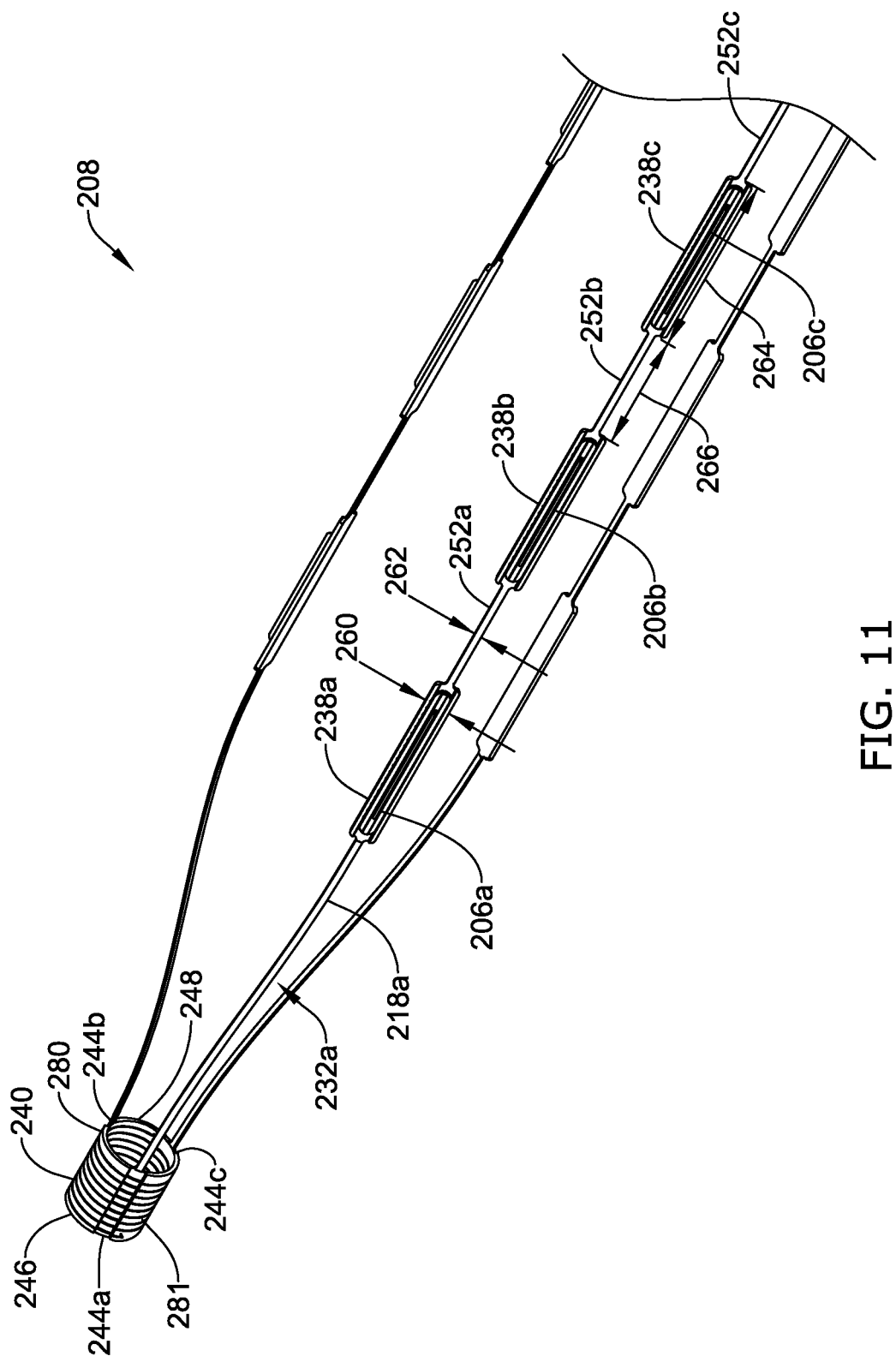
FIG. 11 is an enlarged perspective view of the proximal end region of the illustrative expandable frame of FIG. 10.

The proximal collar 281 and/or the distal collar 283 may include one or more circumferentially extending cuts 240, 242 to form a resilient or spring-like ring element 280, 282. The spring-like elements 280, 282 may allow for bending and/or flexing at or near the proximal and/or distal end sections 224, 226 of the expandable frame 208 which may facilitate navigation within the vasculature. While the expandable frame 208 is illustrated as including both a proximal spring-like ring element 280 and a distal spring-like ring element 282, it is contemplated that only one spring element 280, 282 or no spring elements 280, 282 may be provided. Referring additionally to FIG. 11, which illustrates an enlarged perspective view of the proximal end region 220 of the expandable frame 208, the proximal spring element 280 may have a generally tubular configuration. For brevity, the structure of the spring elements 280, 282 are described with respect to the proximal spring element 280. However, it should be understood that, when so provided, the distal spring element 282 may include any of the structural features described with respect to the proximal spring element 280. In the illustrated embodiment, the cut 240 may be generally helical and extend through the thickness of the proximal spring element 280 (e.g., from an outer surface to an inner surface thereof). The cut 240 may extend along an entire length of the proximal spring element 280 or may extend along less than an entire length of the proximal spring element 280, as desired. It is contemplated that a configuration and/or number of cuts 240 may be varied to change the properties of the proximal spring element 280. For example, the pitch of a helical cut 240 and/or the width of material between adjacent winding of the cut 240 may be varied to adjust a strength and/or flexibility of the proximal spring 280. It is further contemplated that the spring elements 280, 282 may be formed from a wound filament or ribbon.

The proximal spring element 280 may include a plurality of channels 244a, 244b, 244c (collectively, 244) extending from a proximal end 246 to a distal end 248 of the proximal spring element 280. In some cases, the channels 244 may extend over less than an entire length of the proximal spring element 280. For example, the channels 244 may extend proximally from the distal end 248 and terminate distal to the proximal end 246 or the channels 244 may extend distally from the proximal end 246 and terminate proximal to the distal end 248. In yet other examples, the channels 244 may extend over an intermediate region of the proximal spring element 280. In some embodiments, the channels 244 may be configured to receive a proximal end region 232 of the struts 218. For example, when the struts 218 are formed as separate components from the spring elements 280, 282, the proximal end region 232 and/or the distal end region 234 may be secured to the spring elements 280, 282 within the channels 244. It is contemplated that the struts 218 may be adhered, glued, brazed, welded, soldered, etc., within the channels 244.

The expandable frame 208 may be secured to the balloon 202 and/or catheter shaft 204 at one end or both ends thereof. For example, the expandable frame 208 may be fixedly secured to the outer tubular member 210 at or adjacent to the proximal spring element 280 while the distal spring element 282 may be axially slidable about the inner tubular member 212 along a longitudinal axis of the catheter 200. This may allow the expandable frame 208 to lengthen (along the longitudinal axis of the catheter 200) when in the collapsed configuration and shorten when in the expanded configuration. The reverse configuration is also contemplated in which the distal spring element 282 is fixedly secured to the inner tubular member 212 while the proximal spring element 280 is free to slide axially along the outer tubular member 210. In some cases, both the proximal spring element 280 and the distal spring element 282 may be fixedly secured to the catheter 200. It is contemplated that the spring elements 280, 282 may allow the expandable frame 208 to shorten as the balloon 202 is expanded and elongate when the balloon 202 is collapsed, even when both spring elements 280, 282 are coupled to the catheter 200. In other cases, both the proximal spring element 280 and the distal spring element 282 may be free to slide relative to the catheter 200. It is further contemplated that the expandable frame 208 may be coupled (additionally or alternatively to the proximal and/or distal spring elements 280, 282) at locations other than the proximal or distal spring elements 280, 282, as desired.

Referring briefly to FIG. 9, in some cases, one or more elastomeric or flexible bands 250a, 250b, 250c, 250d (collectively, 250) may be circumferentially positioned over the struts 218 and over an outer surface of the balloon 202 to limit circumferential and/or radial movement of the struts 218. For example, a plurality of bands 250, each of which extends circumferentially around the balloon 202, may be positioned at spaced apart locations along the length of the balloon 202. The bands 250 may be axially arranged to reside between adjacent cutting members 206. The struts 218 may be sandwiched between an inner surface of the bands 250 and an outer surface of the balloon 202. The bands 250 may retain the struts in circumferentially spaced apart locations around the balloon 202 to help prevent the struts 218 from crossing over each other. The bands 250 may be held in tension even with the balloon 202 in a fully deflated state such that the bands 250 continuously apply a radially inward force against the struts 218 to push the struts 218 against the deflated balloon 202. The bands 250 may be flexible so as to stretch and continue to apply a radially inward force on the struts 218 as the balloon 202 is expanded. It is further contemplated that the bands 250 may return to their smaller, delivery configuration when the balloon 202 is deflated.

Returning to FIGS. 11 and 12, the mounting modules 238 may be interconnected by rails 252a-i (collectively, 252). In some embodiments, the struts 218 are formed from a single monolithic structure such that the mounting modules 238 and the rails 252 are formed as a single structure. The mounting modules 238 may have a first width 260 and the rails 252 may have a second width 262 smaller than the first width 260. In some cases, the mounting modules 238 may have a width 260 in the range of about 0.01 inches (in) (0.254 mm) to about 0.05 in (1.27 mm), about 0.02 in (0.508 mm) to about 0.04 in (1.016 mm), or about 0.03 in (0.762 mm). The rails 252 may have width 262 in the range of about 0.004 in (0.102 mm) to about 0.012 in (0.305 mm), about 0.006 in (0.152 mm) to about 0.010 in (0.254 mm), or about 0.008 in (0.203 mm). The thinner rails 252 may pivotably couple adjacent mounting modules 238. For example, the rails 252 may bend, flex, and/or pivot relative to the mounting modules 238 such that the expandable frame 208 may move between a collapsed generally linear configuration and an expanded configuration generally conforming to an outer shape of the balloon 202.

In some embodiments, the mounting modules 238 may have a length 264 that is longer than a length 266 of the rails 252, although this is not required. It is contemplated that the length (and/or width) of the mounting modules 238 may be selected to support the desired cutting member 206. In some embodiments, the mounting modules 238 may have a length in the range of about 0.100 in (2.540 mm) to about 0.372 in (9.449 mm), about 0.168 in (4.267 mm) to about 0.304 in (7.722 mm), or about 0.236 in (5.994 mm). The rails 252 may have a length in the range of about 0.100 in (2.540 mm) to about 0.214 in (5.436 mm), about 0.128 in (3.251 mm) to about 0.186 in (4.724 mm), or about 0.157 in (3.988 mm).

Figure 12:
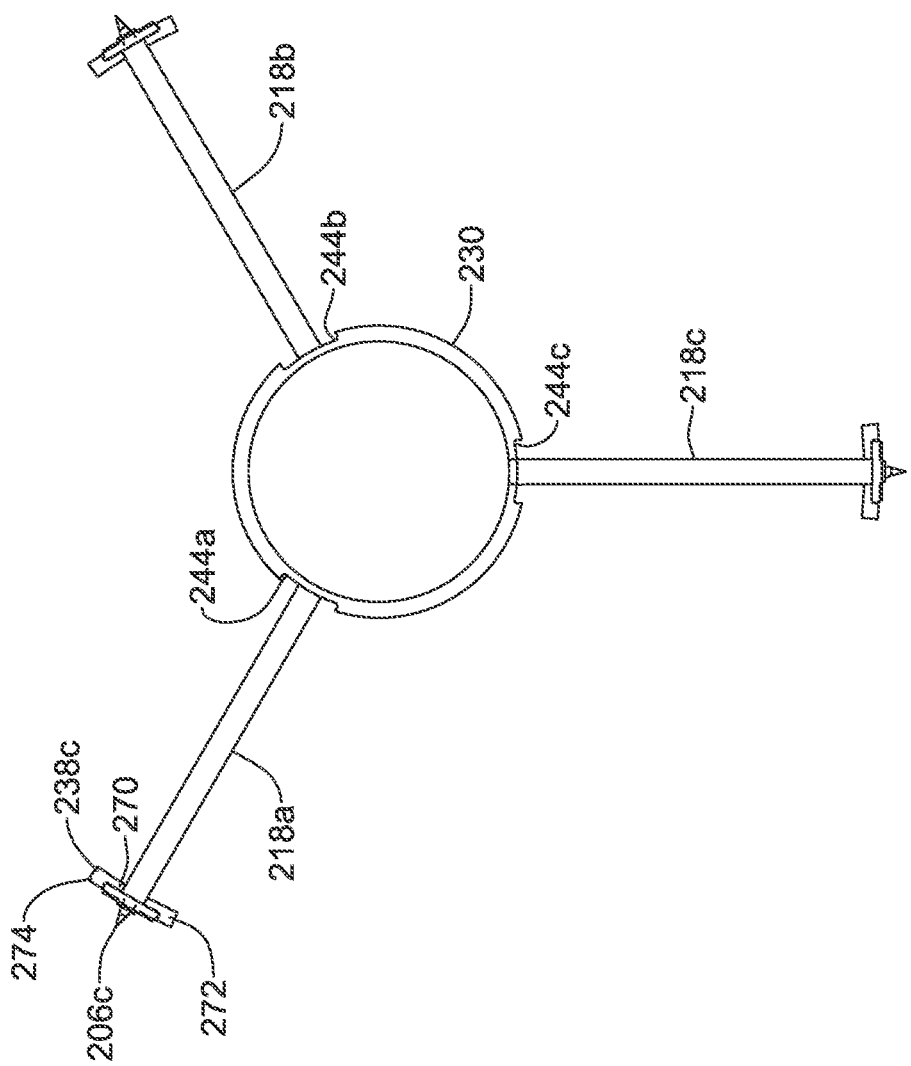
FIG. 12 is a cross-sectional view of the illustrative expandable frame of FIG. 10 taken at line 12-12.

FIG. 12 illustrates a cross-sectional view of the illustrative expandable frame 208 taken at line 12-12 of FIG. 10. The mounting modules 238 may each be configured to receive or carry a cutting member 206. However, it is not required for each mounting module 238 to include a cutting member 206. The mounting module 238 may include a generally U-shaped structure having a bottom wall 270, a first side wall 272 extending generally orthogonally from the bottom wall 270, and a second side wall 274 extending generally orthogonally from the bottom wall 270 and spaced from the first side wall 272. Together, the side walls 272, 274 and the bottom wall 270 may from a channel or trough for receiving the cutting member 206. The cutting member 206 may be adhesively secured to the mounting module 238 within the trough. Other securing techniques may be used as desired, including but not limited to, soldering, brazing, welding, etc. In other embodiments, the cutting member 206 may be formed as a single monolithic structure with the mounting module 238.

Figure 13:
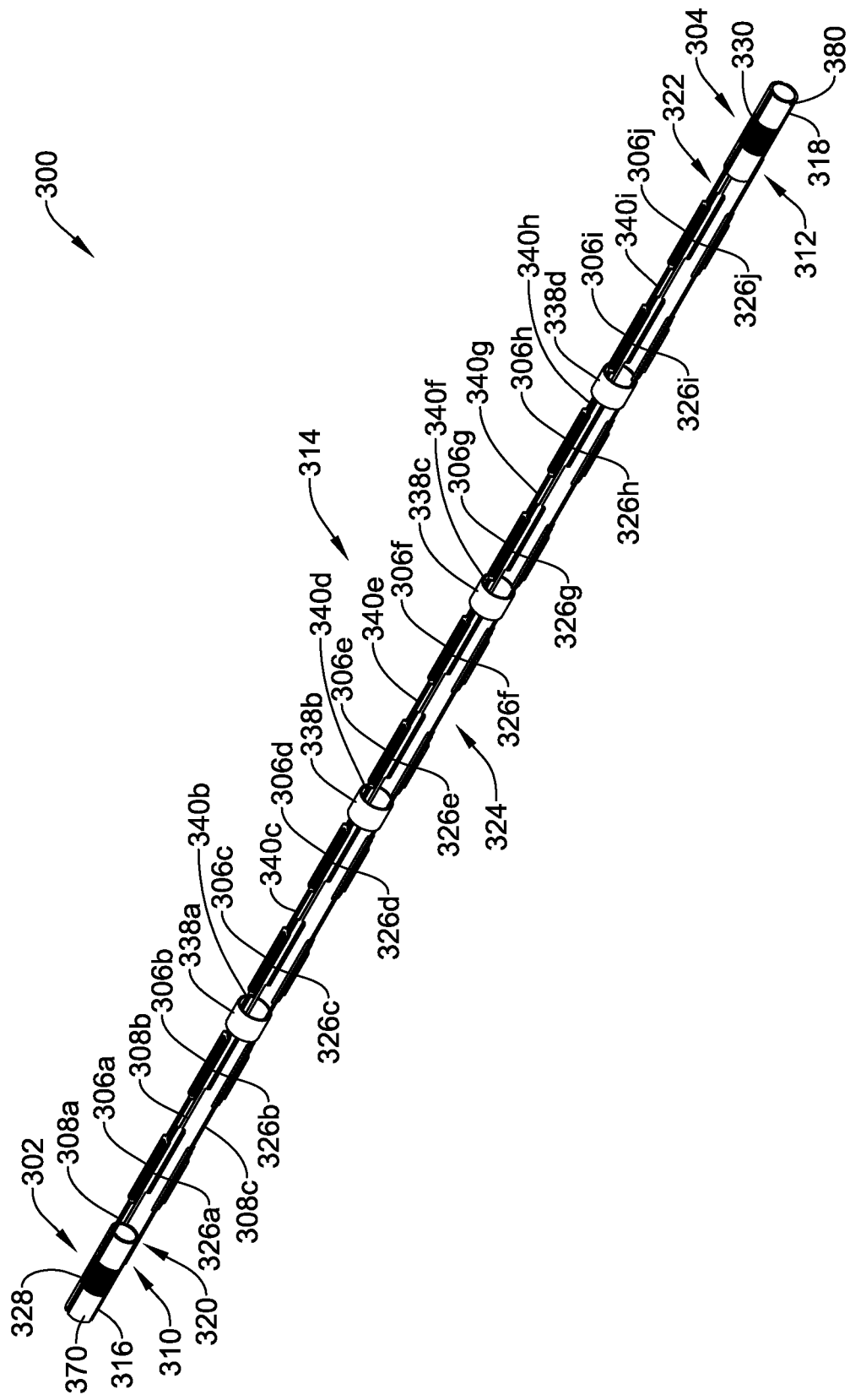
FIG. 13 is a perspective view of another illustrative expandable frame for use with the cutting balloon catheter.

FIG. 13 is a perspective view of another illustrative expandable frame 300 for mounting one or more cutting members 306a-j (collectively, 306) relative to an expandable balloon. The expandable frame 300 may include a plurality of struts 308a, 308b, 308c (collectively, 308) extending axially along a longitudinal axis of the frame 300 from a proximal end region 302 to a distal end region 304. While the expandable frame 300 is illustrated as having three struts 308, it is contemplated that the frame 300 may include any number of struts 308 desired, such as, but not limited to, one, two, three, four, or more. In some embodiments the struts 308 may be configured to be uniformly positioned about a circumference of a balloon. For example, the struts 308 may be configured to have an (or approximately) even or equal spacing between adjacent struts 308. Alternatively, the struts 308 may be eccentrically positioned about the circumference of the balloon. For example, the struts 308 may have unequal spacing between adjacent struts 308.

The expandable frame 300 may have a proximal section 310, a distal section 312, and an intermediate region 314. The expandable frame 300 may be laser cut from a straight metallic tube (e.g., a hypotube) to form a proximal collar 370, a distal collar 380, and the plurality of struts 308 therebetween. In other instances, the proximal section 310, the distal section 312, and/or intermediate section 314 may be cut from a flat sheet and rolled into the desired shape. In yet other embodiments, the proximal collar 370, distal collar 380 and/or struts 308 may be individually formed from a variety of methods and subsequently coupled together. The proximal section 310 and/or the distal section 312 may be formed from spring steel or nitinol and heat set or stress relieved in a collapsed configuration, as shown in FIG. 13. However, other materials may be used, as desired. The proximal section 310 and the distal section 312 of the expandable frame 300 may be moved from the collapsed configuration into an expanded configuration through inflation and thus radial expansion of the balloon, the expanded configuration generally conforming to an outer profile of the balloon.

Each strut 308 of the expandable frame 300 may include a proximal end region 320a, 320b, 320c (collectively, 320), a distal end region 322a, 322b, 322c (collectively, 322), and an intermediate region 324a, 324b, 324c (collectively, 324) disposed therebetween. As described herein, the struts 308 may be individually cut from a flat sheet or cut from a straight metallic tube (e.g., a hypotube), as desired. In some embodiments, the struts 308 may be formed as a monolithic structure. The proximal end regions 320 and/or the distal end regions 322 may be formed from spring steel or nitinol and heat set or stress relieved in a collapsed configuration (not explicitly shown). However, other materials may be used, as desired. In some cases, the proximal end regions 320 and/or the distal end regions 322 may be pivotably coupled with the intermediate regions 324. For example, the proximal end regions 320 and/or the distal end regions 322 may bend, flex, and/or pivot relative to the intermediate regions 324 such that the expandable frame 300 may move between a collapsed generally linear configuration and an expanded configuration generally conforming to an outer shape of the balloon. For example, the pivotable linkage between the proximal end regions 320 and the intermediate regions 324 as well as the pivotable linkage between the distal end regions 322 and the intermediate section 324 may allow the intermediate section 324 to extend generally parallel to a longitudinal axis of the balloon while the proximal and distal end regions 320, 322 extend at a nonparallel angle to the longitudinal axis of the balloon for at least a portion of their respective lengths.

Each strut 308 may include a plurality of links or mounting modules 326a-j (collectively 326) with each mounting module carrying a cutting member 306. While each strut 308 is illustrated as including ten mounting modules 326, it is contemplated that the struts 308 may include fewer than ten or more than ten mounting modules 326 to form a cutting member system having the desired cutting length. In some cases, the mounting modules 326 may be pivotably coupled to one another, the proximal end region 320, and/or the distal end region 322. For instance, the mounting modules 326 may be separate structures linked or coupled together, or the mounting modules 326 may be formed as a single monolithic or unitary structure with living hinges. Alternatively, or additionally, the intermediate region 324 may include a combination of struts 308 having either a unitary structure including a plurality of mounting modules 326 or a plurality of coupled individual mounting modules 326.

Figure 14:
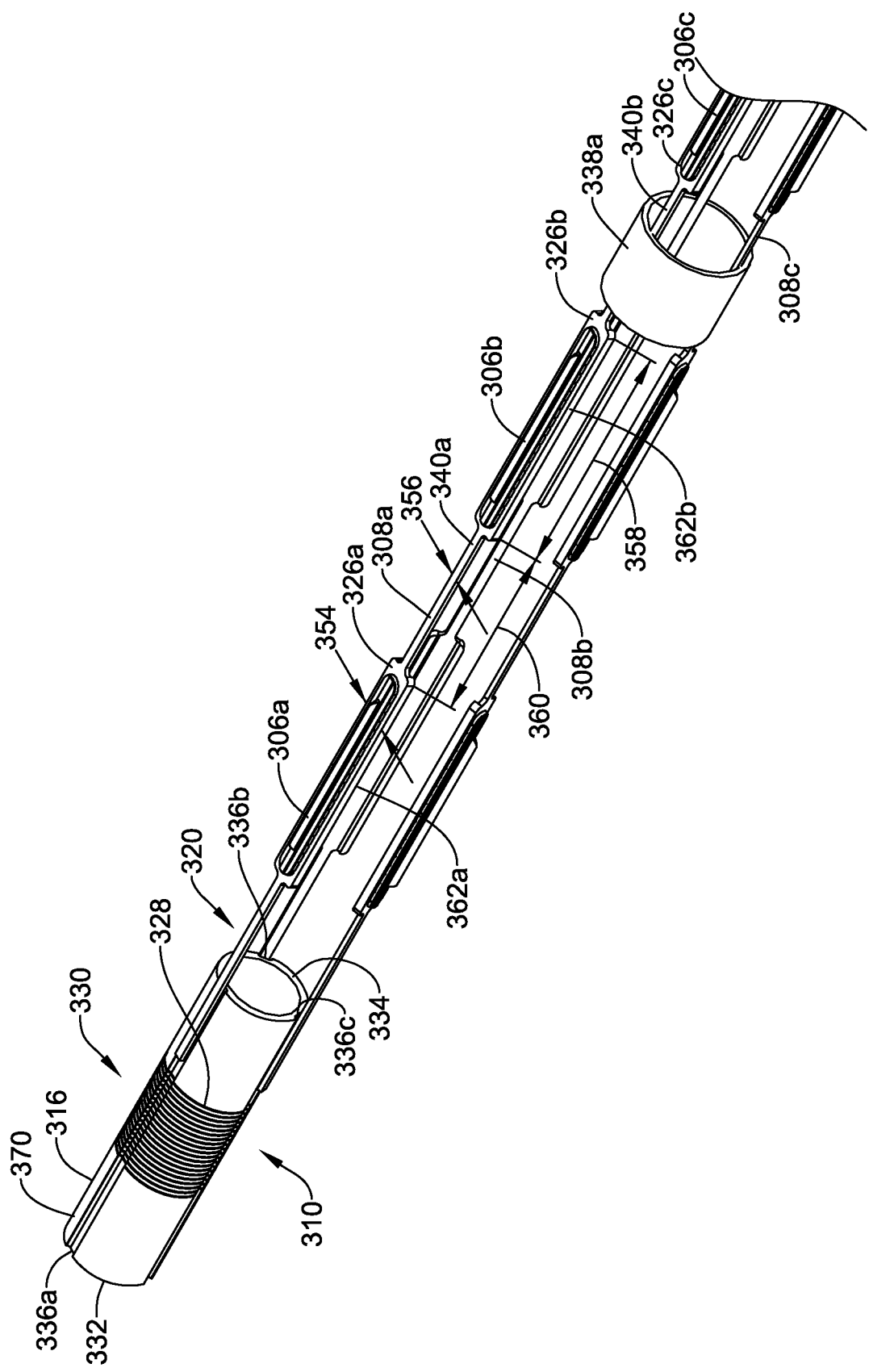
FIG. 14 is an enlarged perspective view of the proximal end region of the illustrative expandable frame of FIG. 13.

The proximal collar 370 and/or the distal collar 380 may include one or more circumferentially extending cuts 328, 330 to form a resilient or spring-like ring element 316, 318. The spring-like elements 316, 318 may allow for bending and/or flexing at or near the proximal and/or distal end regions 310, 312 of the expandable frame 300 which may facilitate navigation within the vasculature. While the expandable frame 300 is illustrated as including both a proximal spring-like ring element 316 and a distal spring-like ring element 318, it is contemplated that only one spring element 316, 318 or no spring elements 316, 318 may be provided. Referring additionally to FIG. 14, which illustrates an enlarged perspective view of the proximal end region 310 of the expandable frame 300, the proximal spring element 316 may have a generally tubular configuration. For brevity, the structure of the spring elements 316, 318 are described with respect to the proximal spring element 316. However, it should be understood that, when so provided, the distal spring element 318 may include any of the structural features described with respect to the proximal spring element 316. In the illustrated embodiment, the cut 328 may be generally helical and extend through the thickness of the proximal spring element 316 (e.g., from an outer surface to an inner surface thereof). The cut 328 may extend along an entire length of the proximal spring element 316 or may extend along less than an entire length of the proximal spring element 316, as desired. For example, in the illustrated embodiment, the cut 328 extends over an intermediate or central region 332 of the proximal spring element 316. It is contemplated that a configuration and/or number of cuts 328 may be varied to change the properties of the proximal spring element 316. For example, the pitch of a helical cut 328 and/or the width of material between adjacent winding of the cut 328 may be varied to adjust a strength and/or flexibility of the proximal spring 316. It is further contemplated that the spring elements 316, 318 may be formed from a wound filament or ribbon.

The proximal spring element 316 may include a plurality of channels 336a, 336b, 336c (collectively, 336) extending from a proximal end 332 to a distal end 334 of the proximal spring element 316. In some cases, the channels 336 may extend over less than an entire length of the proximal spring element 316. For example, the channels 336 may extend proximally from the distal end 334 and terminate distal to the proximal end 332 or the channels 336 may extend distally from the proximal end 332 and terminate proximal to the distal end 334. In yet other examples, the channels 336 may extend over an intermediate region of the proximal spring element 316. In some embodiments, the channels 336 may be configured to receive a proximal end region 320 of the struts 308. For example, when the struts 308 are formed as separate components from the spring elements 316, 318, the proximal end region 320 and/or the distal end region 322 may be secured to the spring elements 316, 318 within the channels 336, as illustrated in FIGS. 13 and 14. It is contemplated that the struts 308 may be adhered, glued, brazed, welded, soldered, etc., within the channels 336.

The expandable frame 300 may be secured to the balloon and/or catheter shaft at one end or both ends thereof. For example, the expandable frame 300 may be fixedly secured to an outer tubular member at or adjacent to the proximal spring element 316 while the distal spring element 318 may be axially slidable about an inner tubular member along a longitudinal axis of the catheter. This may allow the expandable frame 300 to lengthen (along the longitudinal axis of the catheter) when in the collapsed configuration and shorten when in the expanded configuration. The reverse configuration is also contemplated in which the distal spring element 318 is fixedly secured to the inner tubular member while the proximal spring element 316 is free to slide axially along the outer tubular member. In some cases, both the proximal spring element 316 and the distal spring element 318 may be fixedly secured to the catheter. It is contemplated that the spring elements 316, 318 may allow the expandable frame 300 to shorten as the balloon is expanded and elongate when the balloon is collapsed, even when both spring elements 316, 318 are coupled to the catheter. In other cases, both the proximal spring element 316 and the distal spring element 318 may be free to slide relative to the catheter. It is further contemplated that the expandable frame 300 may be coupled (additionally or alternatively to the proximal and/or distal spring elements 316, 318) at locations other than the proximal or distal spring elements 316, 318, as desired.

Referring additionally to FIG. 13, in some cases, one or more elastomeric or flexible bands 338a, 338b, 338c, 338d (collectively, 338) may be circumferentially positioned over the struts 308 and may be configured to be disposed over an outer surface of the balloon to limit circumferential and/or radial movement of the struts 308. For example, a plurality of bands 338, each of which extends circumferentially around the balloon, may be positioned at spaced apart locations along the length of the balloon. The bands 338 may be axially arranged to reside between adjacent cutting members 306. The struts 308 may be sandwiched between an inner surface of the bands 338 and an outer surface of the balloon. The bands 338 may retain the struts in circumferentially spaced apart locations around the balloon to help prevent the struts 308 from crossing over each other. The bands 338 may be held in tension even with the balloon in a fully deflated state such that the bands 338 continuously apply a radially inward force against the struts 308 to push the struts 308 against the deflated balloon. The bands 338 may be flexible so as to stretch and apply a radially inward force on the struts 308 as the balloon is expanded. It is further contemplated that the bands 338 may return to their smaller, delivery configuration when the balloon is deflated.

The mounting modules 326 may be interconnected by rails 340a-i (collectively, 340). In some embodiments, the struts 308 are formed from a single monolithic structure such that the mounting modules 326 and the rails 340 are formed as a single structure. The rails 340 may provide a living hinge between adjacent mounting modules 326, permitting adjacent mounting modules 326, and thus cutting members 306, to pivot relative to one another. The mounting modules 326 may have a first width 354 and the rails 340 may have a second width 356 smaller than the first width 354. In some cases, the mounting modules 326 may have a width 354 in the range of about 0.01 inches (in) (0.254 mm) to about 0.05 in (1.27 mm), about 0.02 in (0.508 mm) to about 0.04 in (1.016 mm), or about 0.03 in (0.762 mm). The rails 340 may have width 356 in the range of about 0.004 in (0.102 mm) to about 0.012 in (0.305 mm), about 0.006 in (0.152 mm) to about 0.010 in (0.254 mm), or about 0.008 in (0.203 mm). The thinner rails 340 may pivotably couple adjacent mounting modules 326. For example, the rails 340 may bend, flex, and/or pivot relative to the mounting modules 326 such that the expandable frame 300 may move between a collapsed generally linear configuration and an expanded configuration generally conforming to an outer shape of the balloon.

In some embodiments, the mounting modules 326 may have a length 358 that is longer than a length 360 of the rails 340, although this is not required. It is contemplated that the length (and/or width) of the mounting modules 326 may be selected to support the desired cutting member 306. In some embodiments, the mounting modules 326 may have a length 358 in the range of about 0.100 in (2.540 mm) to about 0.372 in (9.449 mm), about 0.168 in (4.267 mm) to about 0.304 in (7.722 mm), or about 0.236 in (5.994 mm). The rails 340 may have a length 360 in the range of about 0.100 in (2.540 mm) to about 0.214 in (5.436 mm), about 0.128 in (3.251 mm) to about 0.186 in (4.724 mm), or about 0.157 in (3.988 mm).

The mounting modules 326 may each be configured to receive or carry a cutting member 306. However, it is not required for each mounting module 326 to include a cutting member 306. The mounting module 326 may include a generally planar structure having a bottom wall 362a, 362b (collectively, 362) (see, for example, FIG. 14). The cutting member 306 may be adhesively secured to the mounting module 326 on the planar bottom wall 362. Other securing techniques may be used as desired, including but not limited to, soldering, brazing, welding, etc. In other embodiments, the cutting member 306 may be formed as a single monolithic structure with the mounting module 326.

In some embodiments, the catheter 10, the balloon 16, the expandable frame 36, the expandable frame 100, the expandable frame 208, the expandable frame 300, and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel.

One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the catheter 10, the balloon 16, the expandable frame 36, the expandable frame 100, the expandable frame 208, the expandable frame 300, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the catheter 10, the balloon 16, the expandable frame 36, the expandable frame 100, the expandable frame 208, the expandable frame 300, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the catheter 10, the balloon 16, the expandable frame 36, the expandable frame 100, the expandable frame 208, the expandable frame 300, etc. to achieve the same result.

In some embodiments, a degree of Magnetic Resonance Imaging (MRI) compatibility is imparted into the catheter 10, the balloon 16, the expandable frame 36, the expandable frame 100, etc. For example, the catheter 10, the balloon 16, the expandable frame 36, the expandable frame 100, the expandable frame 208, the expandable frame 300, and/or components or portions thereof, may be made of a material that does not substantially distort the image and create substantial artifacts (e.g., gaps in the image). Certain ferromagnetic materials, for example, may not be suitable because they may create artifacts in an MRI image. The catheter 10, the balloon 16, the expandable frame 36, the expandable frame 100, the expandable frame 208, the expandable frame 300, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the catheter 10, the balloon 16, the expandable frame 36, the expandable frame 100, the expandable frame 208, the expandable frame 300, and/or components thereof, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments the catheter 10, the balloon 16, the expandable frame 36, the expandable frame 100, the expandable frame 208, the expandable frame 300, and/or components thereof, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the catheter 10, the balloon 16, the expandable frame 36, the expandable frame 100, the expandable frame 208, the expandable frame 300, and/or components thereof, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the catheter 10, the balloon 16, the expandable frame 36, the expandable frame 100, the expandable frame 208, the expandable frame 300, and/or components thereof, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms. It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:
1. A balloon catheter comprising:
a catheter shaft;
an inflatable balloon secured to a distal portion of the catheter shaft;
an expandable frame disposed over the balloon, the expandable frame comprising a plurality of struts each having a proximal section, a distal section, and an intermediate section, wherein the proximal section includes a coupling mechanism and is pivotably coupled to a first coupling mechanism of the intermediate section, wherein a portion of one of the coupling mechanism of the proximal section and the first coupling mechanism of the intermediate section passes through an aperture of the other one of the coupling mechanism of the proximal section and the first coupling mechanism of the intermediate section, and the distal section includes a coupling mechanism and is pivotably coupled to a second coupling mechanism of the intermediate section, wherein a portion of one of the coupling mechanism of the distal section and the second coupling mechanism of the intermediate section passes through an aperture of the other one of the coupling mechanism of the distal section and the second coupling mechanism of the intermediate section; and
one or more cutting members coupled to the expandable frame.

2. The balloon catheter of claim 1, wherein at least one of a proximal end region or a distal end region of the expandable frame includes a collar.

3. The balloon catheter of claim 2, wherein the collar includes a helical cut extending from an outer surface to an inner surface of the collar.

4. The balloon catheter of claim 3:
wherein the collar includes a first end region, a second end region, and an intermediate region between the first and second end regions, the intermediate region including the helical cut,
wherein the first end region is fixedly secured to the catheter shaft and the second end region is axially slidable relative to the catheter shaft;
and wherein ends of the plurality of struts are fixedly secured to the second end region of the collar.

5. The balloon catheter of claim 1, further comprising a plurality of elastomeric bands circumferentially surrounding the expandable frame at longitudinally spaced apart locations along the balloon.

6. The balloon catheter of claim 5, wherein the plurality of elastomeric bands are in tension when the balloon is in a fully deflated configuration.

7. The balloon catheter of claim 6, wherein the plurality of elastomeric bands apply a radially inward force on the plurality of struts to press the plurality of struts against an outer surface of the balloon.

8. The balloon catheter of claim 1, wherein each intermediate section of the plurality of struts has one or more modular mounts configured to receive the one or more cutting members.

9. The balloon catheter of claim 8, wherein each of the intermediate sections comprises two or more links pivotably coupling adjacent modular mounts together.

10. The balloon catheter of claim 8, wherein each of the intermediate sections comprises two or more rails pivotably coupling adjacent modular mounts together.

11. The balloon catheter of claim 10, wherein each rail of the two or more rails has a width less than a width of the modular mounts.

12. The balloon catheter of claim 1, wherein the cutting member is adhesively secured to the expandable frame.

13. A balloon catheter comprising:
a catheter shaft;
an inflatable balloon secured to a distal portion of the catheter shaft;
an expandable frame disposed over the balloon, the expandable frame comprising:
a first collar positioned at a first end of the balloon;
a second collar positioned at a second end of the balloon;
a plurality of struts extending between the first collar and the second collar, the plurality of struts including a proximal end region, a distal end region, and an intermediate region disposed therebetween; and
at least one cutting member coupled to each strut of the plurality of struts;
wherein the intermediate region is pivotably coupled to the proximal end region and pivotably coupled to the distal end region;
wherein the first collar includes a portion fixedly secured to the catheter shaft and the second collar includes a portion axially slidable relative to the catheter shaft; and
wherein the second collar is a monolithic collar having a first end region, a second end region, and an intermediate region positioned between the first end region and the second end region, the intermediate region having a helical cut extending through a sidewall thereof, wherein the first end region is fixedly secured to the catheter shaft and the second end region is axially slidable relative to the catheter shaft.

14. The balloon catheter of claim 13, wherein each strut of the plurality of struts comprises a monolithic structure.

15. The balloon catheter of claim 13, wherein an axial length of the intermediate region changes when the second end region axially slides relative to the catheter shaft.

16. The balloon catheter of claim 13, wherein ends of the plurality of struts are affixed to the second end region.

17. A balloon catheter comprising:
   a catheter shaft;
   an inflatable balloon secured to a distal portion of the catheter shaft; and
   an expandable frame disposed over the balloon, the expandable frame comprising:
      a proximal collar;
      a distal collar;
      a plurality of struts extending between the proximal collar and the distal collar, each strut having a plurality of links, each link including a channel extending parallel to a longitudinal axis of the link; and
      a cutting member having a base portion inserted into the channel of each link.

18. The balloon catheter of claim 17, wherein each link includes a pair of U-shaped arms having top portions spaced apart by an opening therebetween, wherein the base of the cutting member is positioned below the top portions and a cutting edge of the cutting member extends above the top portions.

19. The balloon catheter of claim 13, wherein the proximal end region includes a coupling mechanism, the intermediate region includes first and second coupling mechanisms, and the distal end region includes a coupling mechanism,
   wherein the intermediate region is pivotably coupled to the proximal end region by either passing the first coupling mechanism of the intermediate region through the coupling mechanism of the proximal end region or passing the coupling mechanism of the proximal end region through the first coupling mechanism of the intermediate region, and
   wherein the intermediate region is pivotably coupled to the distal end region by either passing the second coupling mechanism of the intermediate region through the coupling mechanism of the distal end region or passing the coupling mechanism of the distal end region through the second coupling mechanism of the intermediate region.

* * * * *